United States Patent [19]

Goeddel et al.

[11] Patent Number: 4,801,685
[45] Date of Patent: Jan. 31, 1989

[54] MICROBIAL PRODUCTION OF MATURE HUMAN LEUKOCYTE INTERFERON K AND L

[75] Inventors: David V. Goeddel, Burlingame, Calif.; Sidney Pestka, North Caldwell, N.J.

[73] Assignees: Hoffmann-La Roche Inc., Nutley, N.J.; Genentech, Inc., So. San Francisco, Calif.

[21] Appl. No.: 56,623

[22] Filed: Jun. 1, 1987

Related U.S. Application Data

[63] Continuation of Ser. No. 894,076, Aug. 5, 1986, abandoned, which is a continuation of Ser. No. 293,044, Aug. 14, 1981, abandoned.

[51] Int. Cl.[4] .................. C07K 13/00; C07K 15/26; A61K 45/02; C12P 21/00
[52] U.S. Cl. .................. 530/351; 424/85.7; 435/68; 435/811
[58] Field of Search .................. 424/85; 530/351; 435/68, 811

[56] References Cited

U.S. PATENT DOCUMENTS 4,289,690 9/1981 Pestka et al. .................. 424/85

4,342,832 8/1982 Goeddel et al. .

OTHER PUBLICATIONS

Nagata et al., Nature, vol. 284, pp. 316–320, 1980.
Goeddel et al., Nature, vol. 290, pp. 20–26, 1981.
Torma and Paucher, J. Biol. Chem., vol. 254, pp. 4810–4816, 1976.
Taniguchi et al., Nature, vol. 285, pp. 547–549, 1980.
Rubinstein et al., Proc. Natl. Acad. Sci., vol. 76, pp. 640–644, 1979.
Manter et al., Gene, vol. 10, pp. 1–10, 1980.
Goeddel et al., Nature, 281:544–548 (10/18/79).
Lawn et al. DNA Sequence of Two Closely Linked Human Leukocyte Interferon Genes, Science, vol. 212, Jun. 5, 1981, p. 1159.
Yelverton et al., Nucleic Acid Research, vol. 9, No. 3, 1981, p. 73).

Primary Examiner—Blondel Hazel
Attorney, Agent, or Firm—Jon S. Saxe; George M. Gould; Julie M. Prlina

[57] ABSTRACT

This invention relates to the microbial production, via recombinant DNA technology, of new human leukocyte interferons, Le IF-K and Le IF-L for use in the treatment of viral and neoplastic diseases, and to the means and end products of such production.

6 Claims, 17 Drawing Sheets

FIG. 2

```
                                                                                    -60         -40         -20           +1          20          40
                                                                                     |           |           |            |           |           |
LeIF A  TGAGCCTAAACCTTAGGCTCAACCATTTCAACCAGTCTAGCAGCATCTGCAACATCTACAATGGCCTTGACCTTTGCTTTACTGGTGGCCCTCCTGGTGC
LeIF B                                      TACTAGCTCAGCAGCAGCCTAGCCTAGCAATGGCCTTGACTTTTATTTAATGGTGGCCTAGTGGTGC
LeIF C                        CAAGGTTATCCATCTCAAGTAGCCTAGCAATTTGCAACATCCCAATGGCCCTGTCCTTTCTTTCTTACTTATGGCCTGCTGGTGC
LeIF D                       CAAGGTTCAGAGTCAGCCCATCTCAGCAAGCCCAGAAGTATCTGCAATATCTACGATGGCCTTTACTGATGGTCCTGGTGGTGC
LeIF E                                                                  ACATCCCAATGGCCCTGTCCTTTCTTTACTGATGATGGCCCTGGTGGTGC
LeIF F                                                                  ACATCCCAATGGCCCTGTCCTTTCTTTACTGATGATGGCCCTGGTGGTGC
LeIF G
LeIF H                       CCAAGGGTTCAGTGTTACCCCTCATCAACCAGCCCAGCAGCATCTTCGGGATTCCCAATGGCATTGCCCTTTGCTTTAATGATGGCCCTTGGTGGTGC 60          80         100         120         140
          |           |           |           |           |
LeIF A  TCAGCTGCAAGTCAAGCTGCTCTGTGGGCTGTGATCTGCCTCAAACCCACAGCCTGGGTAGCAGGAGGAGGACCTTGATGCTCCTGGCACAGATGAGGAAAAT
LeIF B  TCAGCTACAAGTCATTCAGCTCTCTGGGCTGTGATCTGCCTCAGATCTCAGACCCACAGCCTGGGTAACACAGGAGGAGGGCCTTGATACTCCTGGCACAAATGCGAAGAAT
LeIF C  TCAGCTACAAATCCATCTGTTCTCTGGGCTGCTCTGGATCTGCCTCAGATCTGCCTCAGACCCACAGCCTGGGTAATAACAGGAGGAGGGCCTTGATACTCCTGGACACAAATGGAAGAAT
LeIF D  TCAGCTGCAAGTCAAGCTGCTCTCTGGGCTGCTCTGGATCTGCCTCAGATCTGCCTCAGGCCCACAGCCTGGGTAACAGGAGGAGGGCCTTGATGCTCCTGGACACAAATGAGCAGAAT
LeIF E      CTGCCTCTGGGCTGCTGAATCCATCTGTTCTCTGGGCTGTGATCTGCCTCAGGCCCACAGCCTGGGTAACAGGAGGAGGGCCTTCATACTCCTGACACAAATGAGGAGAAT
LeIF F  TCAGCTACAAATCCATCCAGCTGTTCTCTGGGCTGTGATCTGCCTGTAATCTGTCTCAAACCCACAGCCTGAATAACAGGAGGAGGGCCTTGATACTCCTGGCACAAATGGGAAGAAT
LeIF G
LeIF H  TCAGCTGCAAGTCAAGCTGCTCTCTGGGCTGTAATCTGTCTCAAACCCACAGCCTGAATAACAGGAGGACTTTGATGTCTCATGGCACAAATGAGGAGAAT 160         180         200         220         240
          |           |           |           |           |
LeIF A  CTCTCCTTTCCTGCTTGAAGGACAGAGACATGACTTTGGATTTCCC     CAGGAGGAGTTT       GGCAACCAGTTCCAAAAGGCTGAAACCATCCCTGTCCT
LeIF B  CTCTCCTTTCCTGCCTGAAGGACAGAGACATGACTTTGAATTCCCC     CAGGAGGAGTTTGATGATAAACAGTTCCAGAAGGCTCAAGCTCATCTCTGTCCT
LeIF C  CTCTCCTTTCCTGCCTGAAGGACAGAGACATGACTTTGATTTCCGAATCCC CAGGAGGAGTTTGATGGCAACCAGTTCCAGAAGGCTCAAGCCATCTCTGTCCT
LeIF D  CTCTCCTTCCCCGTCTGATGGACAGAGACATGACTTTGGATTTCCC     CAGGAGGAGTTTGATGGCAACCAGTTCCAGAAGGCTCCAGCCATCTCTGTCCT
LeIF E  CTCTCCTTTTTCTTACCTGCCTGAAGGACAGAGACATGACTTTGGATTTCCCAATCATCAGGTGTTTCATGGCAACCAGTTCCAGAAGGTTCAAGCTACTTCCTTT
LeIF F  CTCTCCTTTCCTGCCTGAAGGACAGAGACATGACTTTGGATTTCCT     CAAGAGGAGTTTGATGGCAACCAGTTCCAGAAGGCTCAAGCCATCTCTGTCCT
LeIF G          CATGACTTTGGATTTCCT     CAGGAGGAGTTTGATGGCAACCAGTTCCAGAAGGCTCAAGCCATCTCTGTCCT
LeIF H  CTCTCCTTTCTCCTGCCTGAAGGACAGAGACATGACTTTGAATTTCCC   CAGGAGGAATTTGATGGCAACCAGTTCCAGAAAGCTCAAGCCATCTCTGTCCT

```
              760               780               800               820               840
               |                 |                 |                 |                 |
LeIF A   GTCCCTTACAGAGGACCATGCTGACTGATCCATTATCTATTATTTAAAATATTATTAACTATTTATTAAAACAACTTATTTTTGTTCAT
LeIF B   GCACTAGTCCCTTACAGATGACCATGCTGACTGATCCATCTATTCATCTTATTTGTTAAAATCTTAAAAICTTTATTAGTAACTATAGGGACTTAAATTAGTTTTGT
LeIF C   TCCTTTACAGATGACCATTCTGATGTCCTCTCTGTCCACCTTTCATCTTGTTCATTCTTGGTTAGTGTAATAAAACATGTCCTTATATTACTC-poly(A)
LeIF D   TGTTCATATAACGTCATGTGCACCTTTACAGATGGATCGTTATCATTGTCTATTGTCTAAATATATTAAACATGTCCTTATATTACTC-poly(A)
LeIF E   CTAGTTCCTTACGGATGATCATGCTGATGGATCTGATGGAICTAATAICTATCTATTTATTTATTTGTCTAAATATTTATTAGAGATTTAAATATTTGTCCATGTATC
LeIF F   CTAGTCCTTACAGATGACCATGCTGATAGATCTAATAICTATCTATCTATTTATTTATTTGTCTAAATATTTATTAGAGATTTAAATATTTGTCCATGTAATT
LeIF G   AAATCTTTACAGATGATCATGCAATCTATCTATCTATTTATTAACTATTTTAAATATTTTATTAATAICTAIATTTAATATTTATTATAAGAT
LeIF H   CTTTACAGATGACCATTCTGATGTCCTCCTTTCATCTGTCTCCTTTTCATCTATATTTATTAACTATTTTATATTTATTTATGTAATATCA 860               880               900               920               940
               |                 |                 |                 |                 |
LeIF A   ATTACGTCATGTGCACCTTTGCACAGTGGTTAATGTAATAAAATATGTCTCTTTGTATTTGGT-poly(A)
LeIF B   CATATATTATATGTGACTTTACAGTTGAACTTTACATGTCTCTATATTTATTATTTGCCATGTTAATTATTTTACTATATT-poly(A)
LeIF C   TGTGGTAATGTAACAATATGTCTTCATATTTACCAATATTAATTCCTTTTCATTAAATTTTACTATAC-poly(A)
LeIF D   ATGTATTTTACTTTGTGGTAATATAACACATGTCTTTATATTTAGTCAATATATTACTTTTTGCTTTTTTCATTAAATTTTACTATTAAAACTTCTAT
LeIF E   ATGTGTACTTTTACATGTGTAATATCAAAATATGTAATCTAATATTAGTCAATATGTCTTATGTTTTGTC-poly(A)
LeIF F   TAAATTATATTTTAAACTTAIGTTGTTCAGGTAATGTAACAATATGTGGCTAATATATTAATTAATTCCTTTTCATTAAATTTTACTATTAAAAATATGTCTTATGTTTTGTC-poly(A)
LeIF G   TGAGTACCTTACATTGGTTAATGTAACAAATATGTCTTCATATTTAGCCAATATATTAATTAATTCCTTTTCATTAAATTTTACTAT-poly(A)

960               980              1000
               |                 |                 |
LeIF B   AATTCTTTATTTATTCTTTAAAATTGAACTCCAACCCATGAATTGTGCAAACTGATTAAAGAATGGATGGT-poly(A)
LeIF F   ATTATTTGGTTATTCTTTAATGATTCTTTAATAAGAAATTCCAAGCCC-poly(A)

FIG. 3-4
```

```
                 S1      S10    S20 S23                                         40
                 |        |      |   |                                            |
LeIF A    MALTFALLVALLVLSCKSSCSVGCDLPQTHSLGSRRTLMLLAQMRKISLFSCLKDRHDFGFPQ
LeIF B    MALTFYLMVALVVLSVLSYKSFSSLGCDLPQTHSLGNRRALILLAQMRRISPFSCLKDRHDFEFPQ
LeIF C    MALSFSLLMAVLVLVLSYKSICSLGCDLPQTHSLGNRRALILLGQMGRISPFSCLKDRHDFGFPQ
LeIF D    MASPFALLMVLVVLSCKSSCSLGCDLPETHSLDNRRTLMLLAQMSRISPSSCLMDRHDFRIPQ
                            LPLGCDLPQAHSVGNRRAFILLTQMRRISPFSYLKDRHDFGFPH
LeIF E    MALSFSLLMAVLVLSYKSICSLGCDLPQTHSLGNRRALILLAQMGRISPFSCLKDRHDFGFPQ
                                                                HDFGFPQ
LeIF G    MALPFSLMMALVVLSCKSSCSLGCNLSQTHSLNNRRTLMLMAQMRRISPFSCLKDRHDFEFPQ
LeIF H
All       MA   F  L    VLS KS  S GC L  THSL  RR L L  QM   IS  SCL DRHDF  PQ

100
           |       50        60        70        80        90      |
LeIF A    EEF-GNQFKAETIPVLHEMIQQIFNLFSTKDSSAAWDETLLDKFYTELYQQLNDLEACVIQG
LeIF B    EEFDDKQFQKAQAISVLHEMIQQTFNLFSTKDSSAALDETLLDEFYIELDQQLNDLEVLCDQE
LeIF C    EEFDGNQFQKAGAISVLHEMIQQTFNLFSTEDSSAAWEQSLLEKFSTELYQQLNDLEACVIQE
LeIF D    EEFDGNQFQKAGAISVLHELIQQTFNLFSTKDSSAAWDEDLLDKFCTELYQQLNDLEACVMQE
          QVFHGNHFQKVQAIFLFHEMMQQTFNLFSTKDSSDTWDETLLDKSYTELYQQLNDMEACVIQE
LeIF E    EEFDGNQFQKAGAISVLHEMIQQTFNLFSTKDSSATWEQSLLEKFSTELNQQLNDLEACVIQE
LeIF G    EEFDGNQFQKAGAISVLHEMIQQTFNLFSTKDSSATWDETLLDKFYTELYQQLNDLEACMMQE
LeIF H    EEFDGNQFQKAGAISVLHEMMQQTFNLFSTKNSSAAWDETLLEKFYIELFQQMNDLEACVIQE
All       EEFD  QFQKA  I  VLHE   QQ FNLF T SSA    LL  F   EL QQ ND E    Q

166
           |       110       120       130       140       150    |
LeIF A    VGVTETPLMKEDSILAVRKYFQRITLYLKEKKYSPCAWEVVRAEIMRSFSLSTNLQESLRSKE
LeIF B    VGVIESPLMYEDSILAVRKYFQRITLYLTEKKYSSCAWEVVRAEIMRSFSLSINLQKRLKSKE
LeIF C    VGVEETPLMNEDSILAVKKYFQRRITLYLTEKKYSPCAWEVVRAEIMRSLSFSTNLQKRLRRKE
LeIF D    ERVGETPLMNVDSILAVKKYFQRITLYLTEKKYSPCSWEAVRAEIMRSLSLSTNLQERLRRKE
LeIF E    VGVEETPLRNVDSILAVKKYFQRITLYLTKKKYSPCAWEVVRAEIMRSFSL*TNLQERLRRKE
LeIF G    VGVEDTPLMNVDSILTVRKYFQRITLYLTEKKYSPCAWEVVRAEIMRSFSLSKIFQERLRRKE
          VGVEETPLMNEDSILAVRKYFQRITLYLMEKKYSPCAWEVVRAEIMRSFSFSTNLQKRLRRKD
LeIF H
All       V   PLM  DSIL V KYF  RITLYL  E KYS CAWEVVRAEIMRS S  S     Q  L  K

FIG. 4
```

```
A                                                                                                      GTATGTTCCCTA
H                                                                                                      GTATGTTCCCTA
I                                                                                                      GTATGTTCCTTA
J                                                                                                      GTATGTTCACTA
C                                                                                                      GTATGTTCACTA

A    TTTAAGGC-TAGGCACAAAGCAAGGTCTTCAGAGAACCTGGAGCCTAAGGTTTAGGCTCACCCATT-TCAACCAGTCTAGCAGCATCTCCAACATCTACA
H    TTTAAGGC-TAGGCACAAAGCAAGGTCTTCAGAGAACCTGGAGCCTAAGGTTTAGGCTCACCCATT-TCAACCAGTCTAGCAGCATCTCCAACATCTACA
I    TTTAAGACCTATGCACAGAGCAAGGTCTTCAGAAAACCTACAACCCAAGGTTCAGTGTTACCCCTCATCAACCAGCCCAGCAGCATCTTCAGGGTTCCCA
J    TTTAAGGCCTATGCACAGAGCAAAGTCTTCAGAAAACCTAGAGGCCAAAGTTCAAGGTTACCCATC-TCAAGTAGCCTAGCAACATTTGCAACATCCCA-
C    TTTAAGACCTATGCACAGAGCAAAGTCTCCAGAAAACCTAGAGGCCACGGTTCAA-GTTACCCACC-TCAGGTAGCCTAGTGATATTTGCAAAATCCCA-

+1                                                                                           100
A    ATGGCCTTGACCTTTGCTTTACTGGTGGCCCTCCTGGTGCTCAGCTGCAAGTCAAGCTGCTCTGTGGGCTGTGATCTGCCTCAAACCCACAGCCTGGGTA
H    ATGGCATTGCCCTTTGCTTTAATGATGGCCCTGGTGGTGCTCAGCTGCAAGTCAAGCTGCTCTCTGGGCTGTAATCTGTCTCAAACCCACAGCCTGAATA
I    ATGGCCCTGTCCTTTTCTTTACTGATGGCCGTGCTGGTGCTCAGCTACAAATCCATCTGTTCTCTAGGCTGTGATCTGCCTCAGACCCACAGCCTGGGTA
J    ATGGCCCGGTCCTTTTCTTTACTGATGGTCGTGCTGGTACTCAGCTACAAATCCATCTGCTCTCTGGGCTGTGATCTGCCTCAGACCCACAGCCTGCGTA
C    ATGGCCCTGTCCTTTTCTTTACTTATGGCCGTGCTGGTGCTCAGCTACAAATCCATCTGATCTCTGGGCTGTGATCTGCCTCAGACCCACACCCTGCGTA

200
A    GCAGGAGGACCTTGATGCTCCTGGCACAGATGAGGAGAATCTCTCTTTTCTCCTGCTTGAAGGACAGACATGACTTTGGATTTCCCCAGGAGGAGTTT--
H    ACAGGAGGACTTTGATGCTCATGGCACAAATGAGGAGAATCTCTCCTTTCTCCTGCCTGAAGGACAGACATGACTTTGAATTTCCCCAGGAGGAATTTGA
I    ATAGGAGGGCCTTGATACTCCTGGCACAAATGGGAAGAATCTCTCCTTTCTCCTGCCTGAAGGACAGACCTGACTTTGGACTTCCCCAGGAGGAGTTTGA
J    ATAGGAGGGCCTTGATACTCCTGGCACAAATGGGAAGAATCTCTCCTTTCTCCTGCTTGAAGGACAGACATGAATTCAGATTCCCAGAGGAGGAGTTTGA
C    ATAGGAGGGCCTTGATACTCCTGGGACAAATGGGAAGAATCTCTCCTTTCTCCTGCCTGAAGGACAGACATGATTTCCGAATCCCCCAGGAGGAGTTTGA

300
A    -GGCAACCAGTTCCAAAAGGCTGAAACCATCCCTGTCCTCCATGAGATGATCCAGCAGATCTTCAATCTCTTCAGCACAAAGGACTCATCTGCTGCTTGG
H    TGGCAACCAGTTCCAGAAAGCTCAAGCCATCTCTGTCCTCCATGAGATGATGCAGCAGACCTTCAATCTCTTCAGCACAAAGAACTCATCTGCTGCTTGG
I    TGGCAACCAGTTCCAGAAGACTCAAGCCATCTCTGTCCTCCATGAGATGATCCAGCAGACCTTCAATCTCTTCAGCACAGAGGACTCATCTGCTGCTTGG
J    TGGCCACCAGTTCCAGAAGACTCAAGCCATCTCTGTCCTCCATGAGATGATCCAGCAGACCTTCAATCTCTTCAGCACAGAGGACTCATCTGCTGCTTGG
C    TGGCAACCAGTTCCAGAAGGCTCAAGCCATCTCTGTCCTCCATGAGATGATCCAGCAGACCTTCAATCTCTTCAGCACAGAGGACTCATCTGCTGCTTGG

400
A    GATGAGACCCTCCTAGACAAATTCTACACTGAACTCTACCAGCAGCTGAATGACCTGGAAGCCTGTGTGATACAGGGGGTGGGGGTGACAGAGACTCCCC
H    GATGAGACCCTCCTAGAAAAATTCTACATTGAACTTTTCCAGCAAATGAATGACCTGGAAGCCTGTGTGATACAGGAGGTTGGGGTGGAAGAGACTCCCC
I    GAACAGAGCCTCCTAGAAAAATTTTCCACTGAACTTTACCAGCAACTGAATAACCTGGAAGCATGTGTGATACAGGAGGTTGGGATGGAAGAGACTCCCC
J    GAACAGAGCCTCCTAGAAAAATTTTCCACTGAACTTTACCAGCAACTGAATGACCTGGAAGCATGTGTGATACAGGAGGTTGGGGTGGAAGAGACTCCCC
C    GAACAGAGCCTCCTAGAAAAATTTTCCACTGAAATTTACCAGCAACTGAATGACCTGGAAGCATGTGTGATACAGGAGGTTGGGGTGGAAGAGACTCCCC
```

FIG.8-1

```
                                                                                                            500
A  TGATGAAGGAGGACTCCATTCTGGCTGTGAGGAAATACTTCCAAAGAATCACTCTCTATCTGAAAGAGAAGAAATACAGCCCTTGTGCCTGGGAGGTTGT
H  TGATGAATGAGGACTCCATCCTGGCTGTGAAGAAATACTTCCAAAGAATCACTCTTTATCTGATGGAGAAGAAATACAGCCCTTGTGCCTGGGAGGTTGT
I  TGATGAATGAGGACTCCATCCTGGCTGTGAGGAAATACTTCCAAAGAATCACTCTTTATCTAACAGAGAAGAAATACAGCCCTTCAGCCTGGGAGGTTGT
J  TGATGAATGAGGACTTCATCCTGGCTGTGAGGAAATACTTCCAAAGAATCACTCTTTATCTAATGGAGAAGAAATACAGCCCTTGTGCCTGGGAGGTTGT
C  TGATGAATGAGGACTCCATCCTGGCTGTGAGGAAATACTTCCAAAGAATCACTCTTTATCTAATAGAGAGGAAATACAGCCCTTGTGCCTGGGAGGTTGT

600
A  CAGAGCAGAAATCATGAGATCTTTTTCTTTGTCAACAAACTTGCAAGAAAGTTTAAGAAGTAAGGAATGAAAACTGGTTCAACATGGAAATGATTTTCAT
H  CAGAGCAGAAATCATGAGATCCCTCTCTTTTTCAACAAACTTGCAAAAAAGATTAAGGAGGAAGGATTGAAAAGTGGTTCATCATGGAAATGATTCTCAT
I  CAGAGCAGAAATCATGAGATCTCTCTCTTTTTCAACAAACTTGCAAAAAAATATTAAGGAGGAAGGATTGAAAACTGGTTCAACATGGCAATGATCCTGAT
J  CAGAGCAGAAATCATGAGATCCTTCTCTTTTTCAACAAACTTGAAAAAAGGATTAAGGAGGAAGGATTGAAAACTGGTTCATCATGGAAATGATTCTCAT
C  CAGAGCAGAAATCATGAGATCCCTCTCGTTTTCAACAAACTTGCAAAAAAGATTAAGGAGGAAGGATTGAAAACTGGTTCAACATGGCAATGATCCTGAT

700
A  TGATTCGTATGCCAGCTCACCTTTTTATGATCTGCCATTTCAAAGACTCATGTTTCTGCTATGACCATGACACGATTTAAATCTTTTCAAATGTTTTTAG
H  TGACTAATACATCATCTCACACTTTCATGAGTTCTTCCATTTCAAAGACTCACTTCTCCTATAACCACCACAAGTTGAATCAAAATTTTCAAATGTTTTC
I  TGACTAATACATTATCTCACACTTTCATGAGTTCCTCCATTTCAAAGACTCACTTCTATAACCACCACGAGTTGAATCAAAATTTTCAAATGTTTTCAGC
J  TGACTAATGCATCATCTCACACTTTCATGAGTTCTTCCATTTCAAAGACTCACTTCTATAACCACCACAAGTTGAATCAAAATTTCCAAATGTTTTCAGG
C  TGACTAATACATTATCTCACACTTTCATGAGTTCTTCCATTTCAAAGACTCACTTCTATAACCACGACGTGTTGAATCAAAATTTTCAAATGTTTTCAGC

800
A  GAGTATTAATCAACATTGTATTCAGCTCTTAAGGCACTAGTCCCTTACAGAGGACCATGCTGACTGATCCATTATCTATTTAAATATTTTTAAAATATTA
H  AGGAGTGTAAAGAAGCATCATGTATACCTGTGCAGGCACTAGTCCTTTACAGATGACCATGCTGATGTCTCCTTTCATCTATTTATTTAAATATTTATTT
I  AGTGTAAAGAAGCGTCGTGTATACCTGTGCAGGCACTAGTACTTTACAGATGACCATGCTGATGTCTCTGTTCATCTATTTATTTAAATATTTATTTAAT
J  AGTGTTAAGAAGCATCGTGTTTACCTGTGCAGGCACTAGTCCTTTACAGATGACCATTCTGATGTCTCCTTTCATCTATTTATTTAAATATTTATTTATT
C  AGTGTAAAGAAGTGTCGTGTATACCTGTGCAGGCACTAGTCCTTTACAGATGACCATTCTGATGTCTCTGTTCATCTTTTGTTTAAATATTTATTTAATT

900
A  TTTATTTAACTATTTATAAAACAACTTATTTTTGTTCATATTTATGTCATGTGCACCTTTGCACAGTGGTTAATGTAATAAAATGTGTTCTTTGTATTTGG
H  ATTTAACTATTTTTATTATTTAAATTATTTTTTATGTTAATATCATGTGTACCTTTACATTGTGGTTAATATAACAAATATGTTCTTCATATTTAGCCAA
I  TATTTTTAAGATTTAAATTATTTTTTTATGTAATATCATGTGTACCTTTACATTGTGGTAATGTAACAATATATGTTCTTCATATTTAGCCAATATATT
J  TAACTATTTTTATTATTTAAATTATTTTTTATGTAATATCATATGTACCTTTACATTGTGGTTAATGTAACAAATATGTTCTTCATATTTAGCCAATATA
C  ATTTTTAAAATTTATGTAATATCATGAGTCGCTTTACATTGTGGTAATGTAACAATATATGTTCTTCATATTTAGCCAATATATTAATTTCCTTTTTCA

1000
A  TAAATTTATTTTGTGTTGTTCATTGAACTTTTGCTATGGAACTTTTGTACTTGTTTATTCTTTAAAATGAAATTCCAAGCCTAATTGTGCAACCTGATTA
H  TATATTAATTTCCTTTTTCATTAAATTTTTACTATACAAAATTTCTGTGTTTGGTATTT
I  AATTTCCTTTTTCATTAAATTTTTACTATACAAAATTTCTTGAGTTTGTTTATTCTTAAGAATAAAATGTCGAGGCTGACTTTACAACCTGACTTAAAAA
J  TTAATTTCCTTTTT CATTAAATTTTTACTATACAAAATTTCTTGTGTTTGTTTATTTTTTAAGATTAAATGCCAAGCCTGACTGTATAACCTGACTTAA
C  TTAAATTTTTACTATACAAAATTTCTTGTGTTTGTTTATTCTTTAAGATAAAATGCCAAGGCTGACTTTACAACCTGACTTAAAAATAGATGATTTAATT
```

AGAAA CGA AAA ACA GAC ATA GAA AGT AAA ACT AGG CAT TTA GAA AAT GGA AAT TAG TAT GT

CAC TAT TTA AGA CCT ATG CAC AGA GCA AAG TCT CCA GAA AAC CTA GAG CCA CTG GTT CAA

S1
                                              MET ALA ARG SER PHE SER

GTT ACC CAC CTC AGG TAG CCT AGT GAT ATT TGC AAA ATC CCA ATG GCC CGG TCC TTT TCT

1
LEU LEU MET VAL VAL LEU VAL LEU SER TYR LYS SER ILE CYS SER LEU GLY CYS ASP LEU

TTA CTG ATG GTC GTG CTG GTA CTC AGC TAC AAA TCC ATC TGC TCT CTG GGC TGT GAT CTG

PRO GLN THR HIS SER LEU ARG ASN ARG ARG ALA LEU ILE LEU LEU ALA GLN MET GLY ARG

CCT CAG ACC CAC AGC CTG CGT AAT AGG AGG GCC TTG ATA CTC CTG GCA CAA ATG GGA AGA

ILE SER PRO PHE SER CYS LEU LYS ASP ARG HIS GLU PHE ARG PHE PRO GLU GLU GLU PHE

ATC TCT CCT TTC TCC TGC TTG AAG GAC AGA CAT GAA TTC AGA TTC CCA GAG GAG GAG TTT

ASP GLY HIS GLM PHE GLN LYS THR GLN ALA ILE SER VAL LEU HIS GLU MET ILE GLN GLN

GAT GGC CAC CAG TTC CAG AAG ACT CAA GCC ATC TCT GTC CTC CAT GAG ATG ATC CAG CAG

THR PHE ASN LEU PHE SER THR GLU ASP SER SER ALA ALA TRP GLU GLN SER LEU LEU GLU

ACC TTC AAT CTC TTC AGC ACA GAG GAC TCA TCT GCT GCT TGG GAA CAG AGC CTC CTA GAA

LYS PHE SER THR GLU LEU TYR GLN GLN LEU ASN ASP LEU GLU ALA CYS VAL ILE GLN GLU

AAA TTT TCC ACT GAA CTT TAC CAG CAA CTG AAT GAC CTG GAA GCA TGT GTG ATA CAG GAG

VAL GLY VAL GLU GLU THR PRO LEU MET ASN GLU ASP PHE ILE LEU ALA VAL ARG LYS TYR

GTT GGG GTG GAA GAG ACT CCC CTG ATG AAT GAG GAC TTC ATC CTG GCT GTG AGG AAA TAC

PHE GLN ARG ILE THR LEU TYR LEU MET GLU LYS LYS TYR SER PRO CYS ALA TRP GLU VAL

TTC CAA AGA ATC ACT CTT TAT CTA ATG GAG AAG AAA TAC AGC CCT TGT GCC TGG GAG GTT

VAL ARG ALA GLU ILE MET ARG SER PHE SER PHE SER THR ASN LEU GLN LYS ARG LEU ARG

GTC AGA GCA GAA ATC ATG AGA TCC TTC TCT TTT TCA ACA AAC TTG CAA AAA AGA TTA AGG

FIG. 10

```
                    END
ARG LYS ASP ***
AGG AAG GAT TGA AAA CTG GTT CAT CAT GGA AAT GAT TCT CAT TGA CTA ATG CAT CAT CTC

ACA CTT TCA TGA GTT CTT CCA TTT CAA AGA CTC ACT TCT ATA ACC ACC ACA AGT TGA ATC

AAA ATT TCC AAA TGT TTT CAG GAG TGT TAA GAA GCA TCG TGT TTA CCT GTG CAG GCA CTA

GTC CTT TAC AGA TGA CCA AGA AAG CAA AAA CAG ACA TA
```

FIG.10A

```
1
CYS ASP LEU PRO GLN THR HIS THR LEU ARG  ASN ARG ARG ALA LEU ILE LEU LEU GLY GLN
TGT GAT CTG CCT CAG ACC CAC ACC CTG CGT  AAT AGG AGG GCC TTG ATA CTC CTG GGA CAA

61
MET GLY ARG ILE SER PRO PHE SER CYS LEU  LYS ASP ARG HIS ASP PHE ARG ILE PRO GLN
ATG GGA AGA ATC TCT CCT TTC TCC TGC CTG  AAG GAC AGA CAT GAT TTC CGA ATC CCC CAG

121
GLU GLU PHE ASP GLY ASN GLN PHE GLN LYS  ALA GLN ALA ILE SER VAL LEU HIS GLU MET
GAG GAG TTT GAT GGC AAC CAG TTC CAG AAG  GCT CAA GCC ATC TCT GTC CTC CAT GAG ATG

181
ILE GLN GLN THR PHE ASN LEU PHE SER THR  GLU ASP SER SER ALA ALA TRP GLU GLN SER
ATC CAG CAG ACC TTC AAT CTC TTC AGC ACA  GAG GAC TCA TCT GCT GCT TGG GAA CAG AGC

241
LEU LEU GLU LYS PHE SER THR GLU ILE TYR  GLN GLN LEU ASN ASP LEU GLU ALA CYS VAL
CTC CTA GAA AAA TTT TCC ACT GAA ATT TAC  CAG CAA CTG AAT GAC CTG GAA GCA TGT GTG

301
ILE GLN GLU VAL GLY VAL GLU GLU THR PRO  LEU MET ASN GLU ASP SER ILE LEU ALA VAL
ATA CAG GAG GTT GGG GTG GAA GAG ACT CCC  CTG ATG AAT GAG GAC TCC ATC CTG GCT GTG

361
ARG LYS TYR PHE GLN ARG ILE THR LEU TYR  LEU ILE GLU ARG LYS TYR SER PRO CYS ALA
AGG AAA TAC TTC CAA AGA ATC ACT CTT TAT  CTA ATA GAG AGG AAA TAC AGC CCT TGT GCC

421
TRP GLU VAL VAL ARG ALA GLU ILE MET ARG  SER LEU SER PHE SER THR ASN LEU GLN LYS
TGG GAG GTT GTC AGA GCA GAA ATC ATG AGA  TCC CTC TCG TTT TCA ACA AAC TTG CAA AAA

481
ARG LEU ARG ARG LYS ASP ***
AGA TTA AGG AGG AAG GAT TGA AAA CTG GTT  CAA CAT GCC AAT GAT CCT GAT TGA CTA ATA

541
CAT TAT CTC ACA CTT TCA TGA GTT CTT CCA  TTT CAA AGA CTC ACT TCT ATA ACC ACG ACG

601
TGT TGA ATC AAA ATT TTC AAA TGT TTT CAG  CAG TGT AAA CAA GTG TCG TGT TAA CCT GTG

661
CAG GCA CTA GTC CTT TAA ACA TCA CCA TTC
```

FIG.10B

Fragment from pBR322

Fragment from pBR322 (d)

MICROBIAL PRODUCTION OF MATURE HUMAN LEUKOCYTE INTERFERON K AND L

This is a continuation of application Ser. No. 894,076 filed Aug. 5, 1986 now abandoned which is a continuation of Ser. No. 293,044 filed Aug. 14, 1981, abandoned.

BACKGROUND OF THE INVENTION

The publications and other materials referred to herein to illuminate the background of the invention and, in particular cases, to provide additional detail respecting its practice are incorporated herein by reference and, for convenience, are numerically referenced in the following text and respectively grouped in the appended bibliography.

Leukocyte Interferon

Human leukocyte interferon was first discovered and prepared in the form of very crude precipitates by Isaacs and Lindenmann (3). Efforts to purify and characterize the material have been ongoing since that time, and have led to the preparation of relatively homogeneous leukocyte interferons derived from normal or leukemic (chronic myelogenous leukemia or "CML") donors' leukocytes (4). These interferons are a family of proteins characterized by a potent ability to confer a virus-resistant state in their target cells (1, 2). In addition, interferon can act to inhibit cell proliferation and modulate immune response. These properties have prompted the clinical use of leukocyte interferon as a therapeutic agent for the treatment of viral infections and malignancies.

Leukocyte interferons have been purified to essential homogeneity (7, 8), and reported molecular weights range from about 17,500 to about 21,000. The specific activity of these preparations is remarkably high, $2 \times 10^8$ to $1 \times 10^9$ units/mg protein, but yields from cell culture methods have been discouragingly low. Nevertheless, advances in protein sequencing techniques have, in our hands, permitted the determination of partial amino acid sequences (4). Elucidation of the glycosylation of various leukocyte interferons is not at present complete, but it is now clear (by virtue of the work reported infra) that differences in glycosylation among family members does not alone account for the spectrum of molecular weights observed. Instead, the leukocyte interferons differ markedly in amino acid composition and sequence, and amino acid homology is, in some cases, less than 80 percent.

While isolation from donor leukocytes has provided sufficient material for partial characterization and limited clinical studies with homogeneous leukocyte interferon, it is a totally inadequate source for the amounts of interferon needed for large scale clinical trials and for broad scale prophylactic and/or therapeutic use thereafter. Indeed, presently clinical investigations employing human leukocyte-derived interferons in antitumor and antiviral testing have principally been confined to crude (<1 percent pure) preparations of the material, and long lead times for the manufacture of sufficient quantities, even at unrealistic price levels, have critically delayed investigation on an expanded front.

Recombinant DNA Technology

With the advent of recombinant DNA technology, the controlled microbial production of an enormous variety of useful polypeptides has become possible. Already in hand are bacteria modified by this technology to permit the production of such polypeptide products such as somatostatin (5), the (component) A and B chains of human insulin (9) and human growth hormone (18). More recently, recombinant DNA techniques have been used to occasion the bacterial production of proinsulin and thymosin alpha 1, an immune potentiating substance produced by the thymus.

Other workers have reported on the obtention of DNA coding for human leukocyte interferon and to resultant proteins having leukocyte interferon activity—cf. Nagata et al., *Nature* 284, 316 (1980); Mantei et al., *Gene* 10, 1 (1980). See also Taniguchi et al., *Nature* 285, 547 (1980).

The workhorse of recombinant DNA technology is the plasmid, a non-chromosomal loop of double-stranded DNA found in bacteria and other microbes, oftentimes in multiple copies per cell. Included in the information encoded in the plasmid DNA is that required to reproduce the plasmid in daughter cells (i.e., a "replicon") and ordinarily, one or more selection characteristics such as, in the case of bacteria, resistance to antibiotics which permit clones of the host cell containing the plasmid of interest to be recognized and preferentially grown in selective media. The utility of plasmids lies in the fact that they can be specifically cleaved by one or another restriction endonuclease or "restriction enzyme", each of which recognizes a different site on the plasmidic DNA. Thereafter heterologous genes or gene fragments may be inserted into the plasmid by endwise joining at the cleavage site or at reconstructed ends adjacent to the cleavage site. DNA recombination is performed outside the cell, but the resulting "recombinant" plasmid can be introduced into it by a process known as transformation and large quantities of the heterologous gene-containing recombinant plasmid obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression.

Expression is initiated in a region known as the promoter which is recognized by and bound by RNA polymerase. In some cases, as in the tryptophan or "trp" promoter preferred in the practice of the present invention, promoter regions are overlapped by "operator" regions to form a combined promoter-operator. Operators are DNA sequences which are recognized by so-called repressor proteins which serve to regulate the frequency of transcription initiation at a particular promoter. The polymerase travels along the DNA, transcribing the information contained in the coding strand from its 5' to 3' end into messenger RNA which is in turn translated into a polypeptide having the amino acid sequence for which the DNA codes. Each amino acid is encoded by a nucleotide triplet or "codon" within what may for present purposes be referred to as the "structural gene", i.e. that part which encodes the amino acid sequence of the expressed product. After binding to the promoter, the RNA polymerase first transcribes nucleotides encoding a ribosome binding site, then a translation initiation or "start" signal (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, in bacteria ordinarily as the mRNA is being formed, and themselves produce the encoded polypeptide, beginning at the translation start signal and ending at the previously mentioned stop signal. The desired product is produced if the sequences encoding the ribosome binding site are positioned properly with respect to the AUG initiator codon and if all remaining codons follow the initiator codon in phase. The resulting product may be obtained by lysing the host cell and recovering the product by appropriate purification from other bacterial protein.

We perceived that application of recombinant DNA technology would be the most effective way of providing large quantities of leukocyte interferon which, despite the absence in material so produced of the glycosylation characteristic of human-derived material, could be employed clinically in the treatment of a wide range of viral and neoplastic diseases.

More particularly, we proposed and have since succeeded in producing mature human leukocyte interferon microbially, by constructing one or more genes therefor which could then be inserted in microbial expression vehicles and expressed under the control of microbial gene regulatory controls.

Our approach to obtaining a first leukocyte gene involved the following tasks:

1. Partial amino acid sequences would be obtained by characterization of leukocyte interferon purified to essential homogeneity, and construct sets of synthetic DNA probes constructed whose codons would, in the aggregate, represent all the possible combinations capable of encoding the partial amino acid sequences.

2. Bacterial colony banks would be prepared containing cDNA from induced messenger RNA. Other induced mRNA that had been radio-labelled would be hybridized to plasmid cDNA from this bank. Hybridizing mRNA would be eluted and tested for translation into interferon in oocyte assay. Plasmid DNA from colonies shown positive for interferon in this manner would be further tested for hybridization to probes made as described in (1) above.

3. Parallel to the approach in part (2) above, induced mRNA-derived cDNA in plasmids would be used to form an independent bank of transformant colonies. The probes of part (1) would be used to prime the synthesis of radio-labelled single stranded cDNA for use as hybridization probes. The synthetic probes would hybridize with induced mRNA as template and be extended by reverse transcription to form induced, radio-labelled cDNA. Clones from the colony bank that hybridized to radio-labelled cDNA obtained in this manner would be investigated further to confirm the presence of a full-length interferon encoding gene. Any partial length putative gene fragment obtained in parts (1) or (2) would itself be used as a probe for the full-length gene.

4. The full-length gene obtained above would be tailored, using synthetic DNA, to eliminate any leader sequence that might prevent microbial expression of the mature polypeptide and to permit appropriate positioning in an expression vehicle relative to start signals and the ribosome binding site of a microbial promoter. Expressed interferon would be purified to a point permitting confirmation of its character and determination of its activity notwithstanding the absence of glycosylation.

5. The interferon gene fragment prepared in the foregoing fashion could itself be used in probing, by hybridization, for other partially homologous leukocyte interferon species.

BRIEF SUMMARY OF INVENTION

Human leukocyte interferons K and L have been discovered and, through recombinant DNA technology, enabled the microbial production of these additional members of the family of homologous leukocyte interferons (sans glycosylation) as mature polypeptides essentially unaccompanied by the corresponding presequence or any portion thereof. They may be directly expressed, recovered and purified to levels fitting for use in the treatment of viral and malignant diseases of animals and man. Family members so far expressed have proven efficacious is in vitro testing and, in the first such demonstration of its kind, in in vivo testing as well, the latter involving the first mature leukocyte interferon to have been microbially produced. The invention comprises the new interferons so produced and means of producing them.

Reference herein to the expression of a "mature leukocyte interferon," connotes the bacterial or other microbial production of an interferon molecule unaccompanied by associated glycosylation and the presequence that (as we have discussed) immediately attends mRNA translation of a human leukocyte interferon genome. Mature leukocyte interferon, according to the present invention, is immediately expressed from a translation start signal (ATG) just before the first amino acid codon of the natural product, in which event the mature polypeptide includes the methionine for which ATG codes without essentially altering its character, or the microbial host may process the translation product to delete the initial methionine. Mature leukocyte interferon could be expressed together with a conjugated protein other than the conventional leader, the conjugate being specifically cleavable in an intra- or extracellular environment. See British Patent Publication No. 2007676A. Finally, the mature interferon could be produced in conjunction with a microbial "signal" peptide which transports the conjugate to the cell wall, where the signal is processed away and the mature polypeptide secreted.

The novel leukocyte interferon proteins identified as Le IF K and Le IF L have been defined by means of determined DNA gene and deductive amino acid sequencing—cf. FIG. 1, for example. It will be understood that for these particular interferons, natural allelic variations exist and occur from individual to individual. These variations may be demonstrated by (an) amino acid difference(s) in the overall sequence or by deletions, substitutions, insertions inversions or additions of (an) amino acid(s) in said sequence. For the leukocyte interferon protein hereof, such allelic variations are included within the scope of the label or term defining such, and thus, this invention.

BRIEF DESCRIPTION OF THE DRAWINGS

FIG. 2 is an autoradiogram showing hybridization of potential Le-IF plasmids with $^{32}$P-labelled synthetic deoxyoligonucleotides.

FIG. 3 depicts the nucleotide sequence (coding strand) of eight gene fragments previously isolated as candidates for use in the expression of leukocyte interferons, respectively designated "A" through "H". The ATG tranlational initiation codon and the termination triplet for each LeIF is underlined. The stop codons or termination triplets are followed by 3' untranslated regions. The included full-length gene for Le-IF "A" is missing one codon found in the others depicted, as indicated in the third "A" line of FIG. 3. 5' untranslated regions precede the leader sequences. As isolated, fragment "E" lacked the full presequence or leader, but included the entire gene for the putative mature Le-IF "E". Fragment G as isolated lacked the full coding sequence.

FIG. 4 is a comparison of the eight previously known Le IF protein sequences predicted from nucleotide sequences. The one letter abbreviations recommended by the IUPAC-IUB Commission on Biochemical Nomenclature are used: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine. The numbers refer to amino acid position (S refers to signal peptide). The dash in the 165 amino acid LeIF A sequence at position 44 is introduced to align the LeIF A sequence with the 166 amino acid sequences of the other LeIFs. The LeIF E sequence was determined by ignoring the extra nucleotide (position 187 of FIG. 3) in its coding region. The asterisks indicate in-phase termination codons. Amino acids common to all LeIFs (excluding the pseudogene LeIF E) are also shown. The underlined residues are amino acids which are also present in human fibroblast interferon.

FIGS. 8 and 9 provide the DNA and amino acid (see FIG. 4 above for the corresponding one letter abbreviations) sequences of five LeIF proteins hereof, including types I and J. In FIG. 9, the asterisk indicates a termination codon and the hyphen a deletion or gap in the sequence.

FIG. 10A provides the DNA and corresponding amino acid sequences of Le IF K.

FIG. 10B provides the DNA and corresponding amino acid sequences of Le IF L.

DESCRIPTION OF THE PREFERRED EMBODIMENTS

A. Microorganisms Employed

Figure 1:
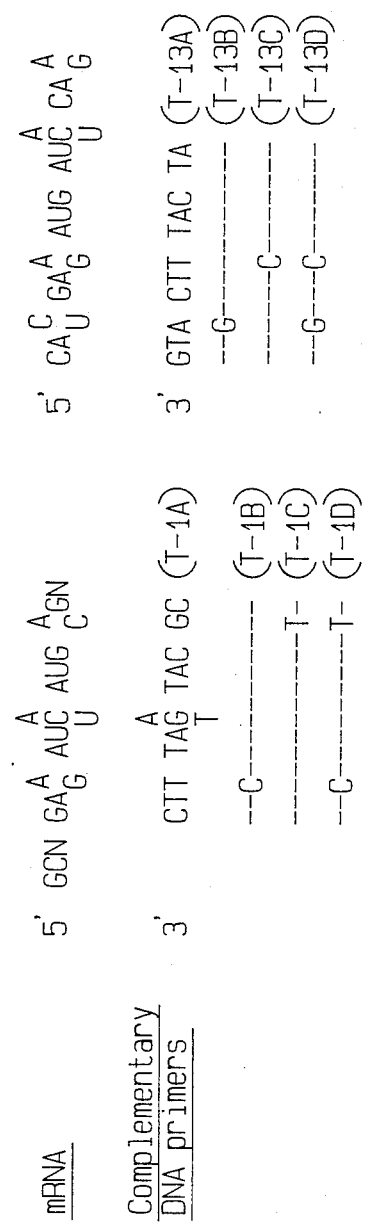
FIG. 1 depicts two series of synthetic deoxynucleotides designated T-1 and T-13 designed to prime cDNA synthesis from leukocyte interferon ("Le-IF") mRNA. Amino acid sequences are given for peptide 1 and a portion of peptide 13 derived from a tryptic digest of human Le-IF $\beta$ (4). All potential mRNA sequences coding for these peptides are shown, as are the corresponding DNA sequences. Here and throughout, the letters A, T, C, G and U respectively connote the nucleotides containing the bases adenine, thymine, guanine, cytosine and uracil, and polynucleotides are depicted as reading from the 5' (left) in the 3' (right) direction and, where double stranded ("d.s.") DNA is depicted, vice-versa for the bottom or non-coding strand.

The work described involved use of two microorganisms: *E. coli* x1776, as described in (11), and *E. coli* K-12 strain 294 (end A, thi$^-$, hsr$^-$, hsm$_k$$^+$), as described in (12). Each has been deposited with the American Type Culture Collection, respectively ATCC accession nos. 31537 and 31446. All recombinant DNA work was performed in compliance with applicable guidelines of the National Institutes of Health.

The invention, in its most preferred embodiments, is described with reference to *E. coli*, including not only strains *E. coli* x1776 and *E. coli* K-12 strain 294, defined above, but also other known *E. coli* strains such as *E. coli* B, or other microbial strains many of which are deposited and (potentially) available from recognized microorganism depository institutions, such as the American Type Culture Collection (ATCC)—cf. the ATCC catalogue listing. See also German Offenlegungsschrift No. 2644432. These other microorganisms include, for example, Bacilli such as *Bacillus subtilis* and other enterobacteriaceae among which can be mentioned as examples *Salmonella typhimurium* and *Serratia marcesans*, utilizing plasmids that can replicate and express heterologous gene sequences therein. Yeast, such as *Saccharomyces cerevisiae*, may also be employed to advantage as host organism in the preparation of the interferon proteins hereof by expression of genes coding therefor under the control of a yeast promoter. (See the copending U.S. patent application Ser. No. 237,213 of Hitzeman et al., filed Feb. 25, 1981, assignee Genentech, Inc. et al., which is incorporated herein by reference.)

B. Source of Le-IF mRNA

Le-IF mRNA may be obtained from human leukocytes, ordinarily those of patients with chronic myelogenous leukemia, that have been induced to produce interferon with Sendai or NDV virus, as described in (4). A particularly preferred source, and that used in the work reported herein, is a cell line designated KG-1 derived from a patient with acute myelogenous leukemia. The cell line, described by Koeffler, H. P. and Golde, D. W., *Science* 200, 1153 (1978), reference (15), grows readily in a culture medium comprising RPMI 1640 plus 10 FCS (heat-inactivated), 25 mM Hepes buffer and 50 μg/ml of gentamicin, and is subcultured 1 to 3 split two times a week. Cells may be frozen from the foregoing growth medium plus 10 dimethyl sulfoxide. KG-1 has been deposited with the American Type Culture Collection, ATCC accession no. CRL 8031.

C. Messenger RNA Purification from KG-1 Cells

KG-1 cells were induced to produce interferon (and leukocyte interferon mRNA) with Sendai or NDV following the procedure described by Rubinstein et al., Proc. Natl. Acad. Sci. USA 76, 640 (1979) and Familetti et al., Methods in Enzymology, (1981) (in press) and (4). Cells were harvested 5 hours after induction and RNA prepared by the guanidine thiocyanate-guanidine hydrochloride procedure (14). RNA from uninduced cells was isolated in the same manner. Oligo (dT)—cellulose chromatography and sucrose gradient ultracentrifugation was used to obtain the 12 S sucrose gradient fraction of poly (A) RNA as described (16, 21). This mRNA had an interferon titer of 8000–10,000 units per microgram in the Xenopus laevis oocyte assay (6).

D. Preparation of Colony Banks Containing Le-IF cDNA Sequences

5 µg of mRNA was used to prepare double stranded cDNA by standard procedures (17, 18). The cDNA was size fractionated by electrophoresis on a 6 polyacrylamide gel and 230 ng of material ranging in size from 500 to 1500 base pairs were recovered by electroelution. A 100 ng portion of this cDNA was tailed with deoxyC residues (19), annealed with 470 ng of plasmid pBR322 (20) which had been tailed with deoxy G residues at the Pst I site, and used to transform E. coli X1776. Approximately 130 tetracycline resistant, ampicillin sensitive transformants were obtained per ng of cDNA.

In a second similar experiment, approximately 1000 tetracycline resistant, ampicillin sensitive E. coli 294 transformants were obtained per ng of cDNA. In this case size fractionated cDNA material ranging in size from 600 to 1300 b.p. was recovered by electroelution for deoxyC tailing.

E. Preparation of Synthetic Oligonucleotides

The amino acid sequences of several tryptic fragments of human leukocyte interferon were determined (4). This information permitted the design of synthetic deoxyoligonucleotides potentially complementary to different regions of LeIF mRNA. The two tryptic peptides T1 and T13 were selected because they had amino acid sequences requiring the synthesis of only 12 and 4 undecamers, respectively, to account for all possible coding sequences (FIG. 1.). Four sets of deoxyoligonucleotide probes were synthesized for each sequence, containing either three (T-1A, B, C, D) or one (T-13A, B, C, D) oligonucleotide each. The indicated complementary deoxyoligonucleotides 11 bases long were chemically synthesized by the phosphotriester method (24). Four individual probes were prepared in the T-13 series. The twelve T-1 probes were prepared in four pools of three probes as shown in FIG. 1.

F. Isolation of Partial Le-IF Gene Fragment Containing Plasmid No. 104

Transformants of E. coli x1776 were screened by the colony hybridization procedure (27) using $^{32}$P-labelled (32) induced mRNA as probe. Unlabelled mRNA from uninduced cells was mixed with the probe at a ratio of 200 to 1 to compete with uninduced mRNA present in the $^{32}$P-labelled preparation. Hybridization of labelled mRNA should occur preferentially to colonies containing induced sequences. Three classes of transformants were obtained. (1) 2–3 of the colonies hybridized to $^{32}$P-mRNA very strongly, (2) 10 hybridized significantly less than class 1, and (3) the remainder gave no detectable hybridization signal. This 3rd class was eliminated from further screening.

The positive colonies were examined for the presence of interferon-specific sequences by an assay which depends upon hybridization of interferon mRNA specifically to plasmid DNA. Initially, 60 strong positive colonies (class 1) were grown individually in 100 ml of M-9 broth (42) supplemented with tetracycline (20 µg/ml), diaminopimelic acid (100 µg/ml), thymidine (20 µg/ml), and d-biotin (1 µg/ml). Ten cultures were pooled and plasmid DNA was isolated from the six pools as described earlier (34, 35). Ten µg of each plasmid DNA pool were cleaved with HindIII, denatured and covalently bound to DBM paper (36). One µg of purified mRNA from induced cells was hybridized to each filter. Unhybridized mRNA was removed by washing. The specifically hybridized mRNA was eluted and translated in Xenopus laevis oocytes. By this assay, all six pools were negative. Five pools of ten colonies each and one pool of nine colonies were made from 59 weakly positive colonies, (class 2) and plasmids were prepared from the pools and examined as above. Among the six pools tested, one (K10) hybridized to interferon mRNA at levels significantly above background levels each time it was tested. In order to identify the specific interferon cDNA clone plasmid DNAs were prepared from the 9 colonies of pool K10 and examined individually. Two of the nine plasmids (No. 101 and No. 104) bound interferon mRNA well above background levels.

G. Preparation and Use of cDNA probes obtained by Synthetic Oligonucleotide Priming of Induced mRNA; Identification of Colonies pL 1-30

A rapid plasmid isolation procedure (22) was used to prepare 1 µg of plasmid DNA from each of 500 individual E. coli 294 transformants. Each DNA sample was denatured and applied to nitrocellulose filters in triplicate following a published procedure (23).

The four individual probes of the T-13 series and the twelve T-1 probes prepared in four pools of three primers each were used to prime the synthesis of radiolabelled single stranded cDNA for use as hybridization probes. The template mRNA was either the 12S RNA from Sendai-induced KG-1 cells (8000 units IF activity per µg) or total poly (A) mRNA from uninduced leukocytes (<10 units per µg). $^{32}$P-labelled cDNA was prepared from these primers using published reaction conditions (25). The 60 µl reactions were performed in 20 mM Tris-HCl (pH 8.3), 20 mM KCl, 8 mM MgCl$_2$, 30 mM β-merceptoethanol. Reactions included one µg of each primer (i.e. 12 µg total for T-1 series, 4 µg total for T-13 series), 2 µg of "induced" 12S fraction mRNA (or 10 µg of uninduced poly (A) mRNA), 0.5 mM dATP, dGTP, dTTP, 200 µCi ($\alpha^{32}$P)dCTP (Amersham, 2–3,000 Ci/mmole), and 60 units reverse transcriptase (Bethesda Research Laboratories). Product was separated from unincorporated label by gel filtration on a 10 ml Sephadex G-50 column, treated with 0.3N NaOH for 30′ at 70° C. to destroy RNA, and neutralized with HCl. Hybridizations were performed as described (23).

The three sets of nitrocellulose filters containing the 500 plasmid samples were hybridized with (a) induced cDNA primed with the T-1 set of primers, (b) T-13 primed induced cDNA, and (c) uninduced cDNA prepared by using both sets of primers. Clones were considered positive if they hybridized more strongly to one or both of the induced cDNA probes than to the total uninduced probe. Thirty "positive" clones (pL1–pL30) were selected from the 500 for further analysis.

H. Selection of Additional "Positive" Colonies pL31–39 using a Restriction Fragment of Plasmid 104

A unique 260 b.p. BglII restriction fragment isolated from the plasmid 104 clone was labelled by a published procedure (26) with $^{32}P$ and used as probe to independently screen 400 E. coli 294 transformants by an in situ colony screening procedure (27). Nine colonies (Pl31–pL39) were identified which hybridized to different extents with this probe. In addition, the labelled 260 bp fragment was used to independently screen 4000 E. Coli 294 transformants in the same manner. 50 colonies were identified which hybridized to different extents with this probe. One contained the Le-IF G fragment, one contained the Le-IF H fragment, and one contained a fragment designated Le-IF H1, an apparent allele of Le-IF H. The hybrid plasmids which result are designated "pLe-IF H", etc.

I. Isolation and DNA Sequencing of a First Full-Length Le-IF Gene Fragment from pL1–39

Plasmid DNA was prepared from all 39 potential Le-IF cDNA clones and rescreened with the same 260 b.p. DNA probe using the dot hybridization procedure (23). Three plasmids (pl4, pL31, pL34) gave very strong hybridization signals, four (pL13, pL30, pL32, pL36) hybridized moderately, and three (L6, pL8, pL14) hybridized weakly with the probe.

The 39 potential Le-IF cDNA recombinant plasmids were also screened by using $^{32}P$-labelled synthetic undecamers (individual T-1 primer pools or individual T-13 primers) directly as hybridization probes. The hybridization conditions were chosen such that perfect base pairing should be required for detectable hybridization signals (28). Thus, plasmid DNA from the 39 clones was prepared by a standard cleared lysate procedure (29) and purified by Biorad Agarose A-50 column chromatography. Samples (3 μg) of each prep were linearized by treatment with Eco RI, denatured in alkali and spotted on 2 separate nitrocellulose filters (1.5 μg per spot) (23). Individual synthetic deoxyoligonucleotide primers and primer pools were phosphorylated with ($\gamma^{32}P$) ATP as follows: 50 pmoles of oligonucleotide and 100 pmoles of ($\gamma^{32}P$)ATP (New England Nuclear, 2500 Ci/mmole) were combined in 30 μl of 60 mM Tris-HCl (pH 8), 10 mM MgCl$_2$, 15 mM β-mercaptothanol. 2 units of T4 polynucleotide kinase were added and, after 30' at 37° C., $^{32}P$ labelled primers were purified by chromatography on 10 ml Sephadex G-50 columns. Hybridizations were performed using $10^6$ cpm of primer T-13C or $3 \times 10^6$ cpm of primer pool T-1C. The hybridizations were performed at 15° C. for 14 hours in 6×SSC, 10X Denhardt's solution, as described by Wallace et al. (28). Filters were washed for 5' (3 times) at 0° C. in 6xSSC, dried, and exposed to x-ray film. Results are shown in FIG. 2 for $^{32}P$ primer pool T-13C and primer T-1C.

Plasmid DNA from clone 104 was found to give significant hybridization with primer pool T-1C and primer T-13C, but no detectable hybridization with the other undecamers. As shown in FIG. 2, several of the 39 potential Le-IF plasmids (pL2, 4, 13, 17, 20, 30, 31, 34) also hybridized with both of these probes. Restriction analysis showed that only one of these plasmids, pL31, also contained a 160 b.p. internal Bgl II fragment. Pst I digestion of pL31 showed the size of the cDNA insert to be approximately 1000 base pairs.

Figure 5:
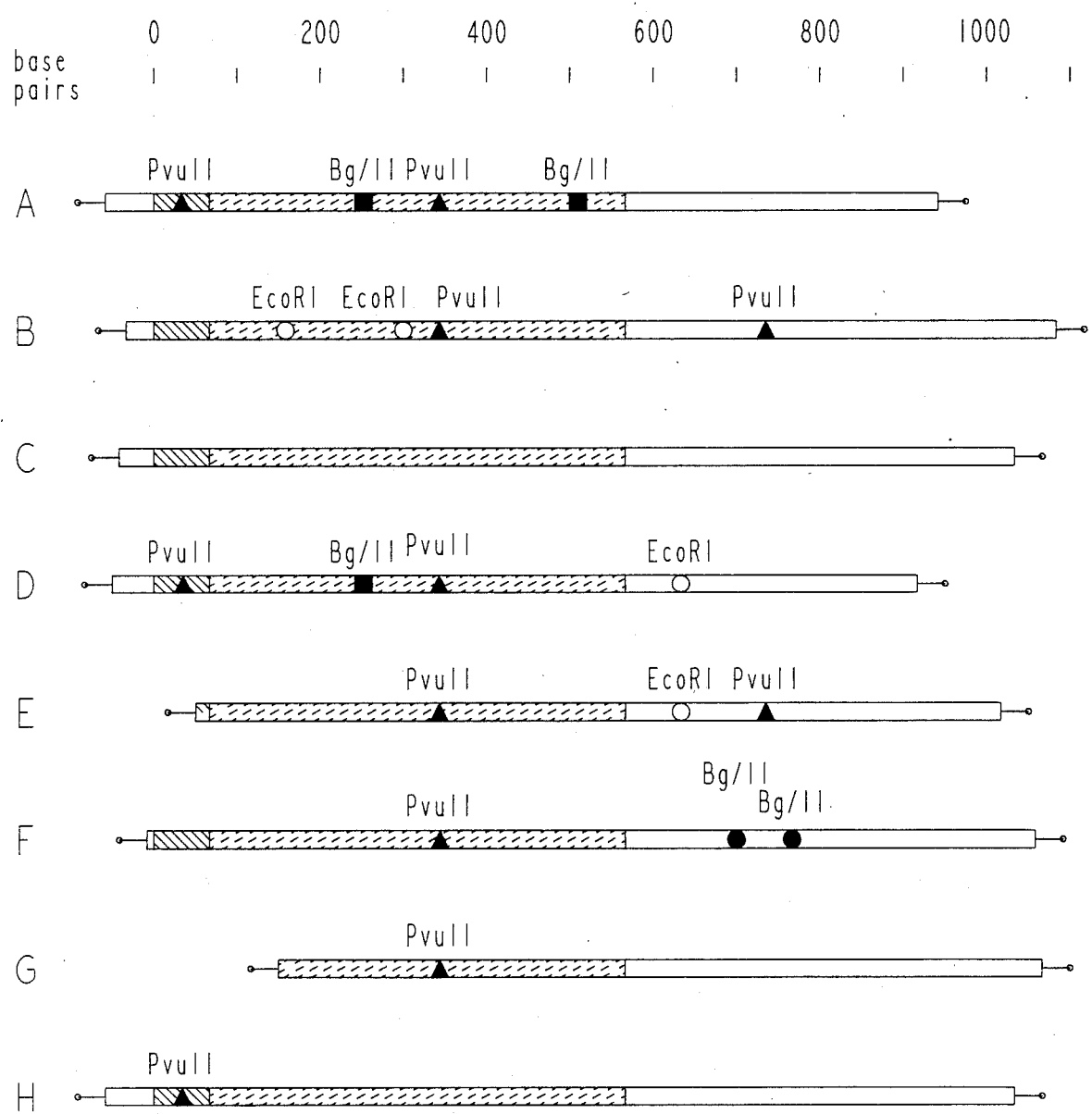
FIG. 5 depicts restriction endonuclease maps of the eight types of LeIF cloned cDNAs (A through H). The hybrid plasmids were constructed by the dC:dG tailing method Goeddel, D. V. et al, *Nature* 287, 411–416 (1980). Therefore, the cDNA inserts can be exised using Pst I. The lines at the end of each cDNA insert represent the flanking homopolymeric dC:dG tails. The positions of Pvu II, Eco RI and Bgl II restriction sites are indicated. Shaded regions of the figure represent the coding sequences of mature LeIFs; the cross-hatched regions indicate signal peptide coding sequences and the open regions show 3' and 5' noncoding sequences.

The entire Pst I insert of pL31 was sequenced by both the Maxam-Gilbert chemical method (30) and by the dideoxy chain termination procedure (31) after subcloning Sau 3a fragments into an M13 vector. The DNA sequence is shown ("A") in FIG. 3. The appropriate translational reading frame could be predicted from protein sequence information in hand (4), the known range of Le-IF molecular weights, and the relative incidence of stop triplets in the three possible reading frames, and that in turn permitted prediction of the entire Le-IF amino acid sequence, including a pre- or signal peptide. The first ATG translational initiation codon is found 60 nucleotides from the 5' end of the sequence and is followed, 188 codons later, by a TGA termination triplet; there are 342 untranslated nucleotides at the 3' end, followed by a poly (A) sequence. The putative signal peptide (presumably involved in the secretion of mature Le-IF from leukocytes) is 23 amino acids long. The 165 amino acids constituting the mature Le-IF have a calculated MW of 19,390. We have termed the Le-IF encoded by pL31 "Le-IF A." It can be seen from the sequence data ("A") in FIG. 5 that the tryptic peptides T1 and T13 of Le-IF B (4)(FIG. 1) corresponds to amino acids 145–149 and 57–61 respectively of Le-IF A. The actual DNA coding sequences found in these two regions are those represented by primer pool T1-C and primer T13-C, as the data shown in FIG. 2 had suggested.

J. Direct Expression of a First Mature Leukocyte Interferon

1. Generally

The procedure followed to express Le-IF a directly as a mature interferon polypeptide was a variant of that earlier employed for human growth hormone (18), insofar as it involved the combination of synthetic (N-terminal) and complementary DNAs.

Figure 6:
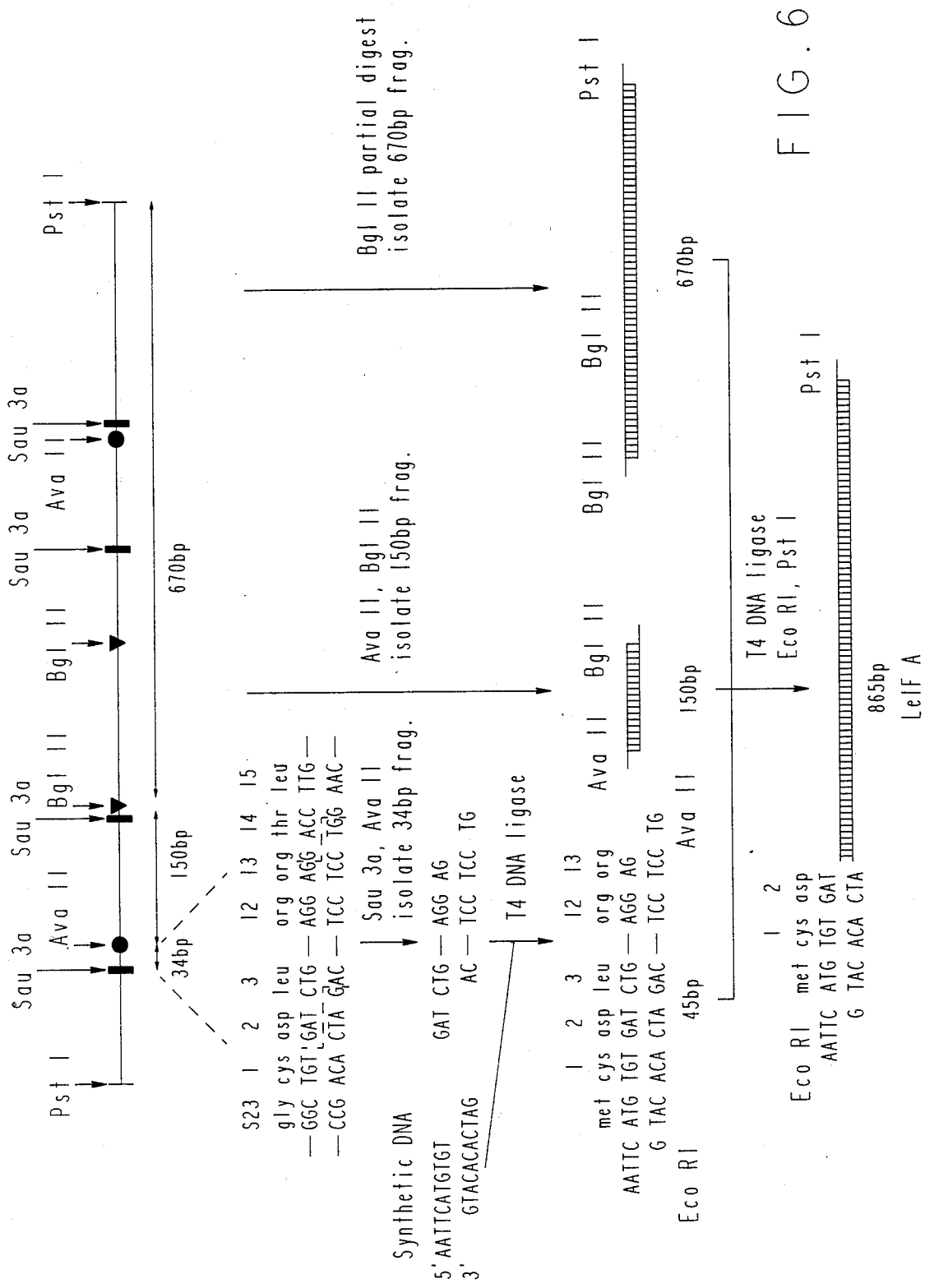
FIG. 6 schematically depicts the construction of a gene coding for the direct microbial synthesis of mature Le-IF A. Restriction sites and residues are as shown ("Pst I", etc.). The term "b.p." connotes "base pair."

As shown in FIG. 6, a Sau 3a restriction endonuclease site is conveniently located between codons 1 and 2 of Le-IF A. Two synthetic deoxyoligonucleotides were designed which incorporate an ATG translational initiation codon, restore the codon for amino acid 1 (cysteine), and create an Eco RI sticky end. These oligomers were ligated to a 34 b.p. 3a-Ava II fragment of pL31. The resulting 45 b.p. product was ligated to two additional DNA fragments to construct an 865 base pair synthetic-natural hybrid gene which codes for Le-IF A and which is bounded by Eco RI and Pst I restriction sites. This gene was inserted into pBR322 between the Eco RI and Pst I sites to give the plasmid pLe-IF A1.

Plasmid pGM1 carries the E. coli tryptophan operon containing the deletion ΔLE1413 (G. F. Miozzari, et al., (1978) J. Bacteriology 133, 1457–1466)) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. The plasmid, 20 μg, was digested with the restriction enzyme PvuII which cleaves the plasmid at five sites. The gene fragments were next combined with EcoRI linkers (consisting of a self complementary oligonucleotide of the sequence: pCATGAATTCATG) providing an EcoRI cleavage site for a later cloning into a plasmid containing an EcoRI site. The 20 μg of DNA fragments obtained from pGM1 were treated with 10 unitsT4 DNA ligase in the presence of 200 pico moles of the 5'-phosphorylated synthetic oligonucleotide pCATGAATTCATG and in 20μl T4 DNA ligase buffer (20 mM tris, pH 7.6, 0.5 mM ATP, 10 mM MgCl2, 5 mM dithiothreitol) at 4° C. overnight. The solution was then heated 10 minutes at 70° C. to halt ligation. The linkers were cleaved by EcoRI digestion and the fragments, now with EcoRI ends were separated using 5 percent polyacrylamide gel electrophoresis (hereinafter "PAGE") and the three largest fragments isolated from the gel by first staining with ethidium bromide, locating the fragments with ultraviolet light, and cutting from the gel the portions of interest. Each gel fragment, with 300 microliters 0.1×TBE, was placed in a dialysis bag and subjected to electrophoresis at 100 v for one hour in 0.1×TBE buffer (TBE buffer contains: 10.8 gm tris base, 5.5 gm boric acid, 0.09 gm Na2EDTA in 1 liter H2O). The aqueous solution was collected from the dialysis bag, phenol extracted, chloroform extracted and made 0.2M sodium chloride, and the DNA recovered in water after ethanol precipitation. The trp promoter-operator-containing gene with EcoRI sticky ends was identified in the procedure next described, which entails the insertion of fragments into a tetracycline sensitive plasmid which, upon promoter-operator insertion, becomes tetracycline resistant.

Plasmid pBRH1 (R. I. Rodriguez, et al., Nucleic Acids Research 6, 3267-3287 [1979]) expresses ampicilin resistance and contains the gene for tetracycline resistance but, there being no associated promoter, does not express that resistance. The plasmid is accordingly tetracycline sensitive. By introducing a promoter-operator system in the EcoRI site, the plasmid can be made tetracycline resistant.

pBRH1 was digested with EcoRI and the enzyme removed by phenol extraction followed by chloroform extraction and recovered in water after ethanol precipitation. The resulting DNA molecule was, in separate reaction mixtures, combined with each of the three DNA fragments obtained above and ligated with T4 DNA ligase as previously described. The DNA present in the reaction mixture was used to transform competent E. coli K-12 strain 294, K. Backman et al., Proc Nat'l Acad Sci USA 73, 4174-4198 [1976]) by standard techniques (V. Hershfield et al., Proc Nat'l Acad Sci USA 71, 3455-3459 [1974]) and the bacteria plated on LB plates containing 20 μg/ml ampicillin and 5 μg/ml tetracycline. Several tetracycline-resistant colonies were selected, plasmid DNA isolated and the presence of the desired fragment confirmed by restriction enzyme analysis. The resulting plasmid is designated pBRHtrp.

An EcoRI and BamHI digestion product of the viral genome of hepatitis B was obtained by conventional means and cloned into the EcoRI and BamHI sites of plasmid pGH6 (D. V. Goeddel et al., Nature 281, 544 [1979]) to form the plasmid pHS32. Plasmid pHS32 was cleaved with XbaI, phenol extracted, chloroform extracted and ethanol precipitated. It was then treated with 1 μl E. coli polymerase I, Klenow fragment (Boehringer-Mannheim) in 30 μl polymerase buffer (50 mM potassium phosphate pH 7.4, 7 mM MgCl2, 1 mM β-mercaptoethanol) containing 0.1 mM dTTP and 0.1 mM dCTP for 30 minutes at 0° C. then 2 hr. at 37° C. This treatment causes 2 of the 4 nucleotides complementary to the 5' protruding end of the XbaI cleavage site to be filled in:

Two nucleotides, dC and dT, were incorporated giving an end with two 5' protruding nucleotides. This linear residue of plasmid pHS32 (after phenol and chloroform extraction and recovery in water after ethanol precipitation) was cleaved with EcoRI. The large plasmid fragment was separated from the smaller EcoRI-XbaI fragment by PAGE and isolated after electroelution. This DNA fragment from pHS32 (0.2 μg), was ligated, under conditions similar to those described above, to the EcoRI-Taq I fragment of the tryptophan operon (~0.01 μg), derived from pBRHtrp.

In the process of ligating the fragment from pHS32 to the Eco RI-Taq I fragment, as described above, the Taq I protruding end is ligated to the XbaI remaining protruding end even though it is not completely Watson-Crick base-paired:

A portion of this ligation reaction mixture was transformed into E. coli 294 cells, heat treated and plated on LB plates containing ampicillin. Twenty-four colonies were selected, grown in 3 ml LB media, and plasmid isolated. Six of these were found to have the XbaI site regnerated via E. coli catalyzed DNA repair and replication:

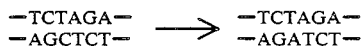

These plasmids were also found to cleave both with EcoRI and HpaI and to give the expected restriction fragments. One plasmid, designated pTrp 14, was used for expression of heterologous polypeptides, as next discussed.

The plasmid pHGH 107 (D. V. Goeddel et al, Nature, 281, 544, 1979) contains a gene for human growth hormone made up of 23 amino acid codons produced from synthetic DNA fragments and 163 amino acid codons obtained from complementary DNA produced via reverse transcription of human growth hormone messenger RNA. This gene, though it lacks the codons of the "pre" sequence of human growth hormone, does contain an ATC translation initiation codon. The gene was isolated from 10 μg pHGH 107 after treatment with EcoRI followed by E. coli polymerase I Klenow fragment and dTTP and dATP as described above. Following phenol and chloroform extraction and ethanol precipitation the plasmid was treated with BamHI.

The human growth hormone ("HGH") gene-containing fragment was isolated by PAGE followed by electroelution. The resulting DNA fragment also contains the first 350 nucleotides of the tetracycline resistance structural gene, but lacks the tetracyline promoter-operator system so that, when subsequently cloned into an expression plasmid, plasmids containing the insert can be located by the restoration of tetracycline resistance. Because the EcoRI end of the fragment has been filled in by the Klenow polymerase I procedure, the fragment has one blunt and one sticky end, ensuring proper orientation when later inserted into an expression plasmid.

The expression plasmid pTrp14 was next prepared to receive the HGH gene-containing fragment prepared above. Thus, pTrp14 was XbaI digested and the resulting sticky ends filled in with the Klenow polymerase I procedure employing dATP, dTTP, dCTP and dCTP. After phenol and chloroform extraction and ethanol precipitation the resulting DNA was treated with BamHI and the resulting large plasmid fragment isolated by PAGE and electroelution. The pTrp14-derived fragment had one blunt and one sticky end, permitting recombination in proper orientation with the HGH gene containing fragment previously described.

The HGH gene fragment and the pTrp14 ΔXba-BamHI fragment were combined and ligated together under conditions similar to those described above. The filled in XbaI and EcoRI ends ligated together by blunt end ligation to recreate both the XbaI and the EcoRI site:

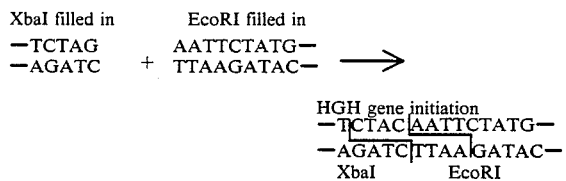

This construction also recreates the tetracycline resistance gene. Since the plasmid pHGH 107 expresses tetracycline resistance from a promoter lying upstream from the HGH gene (the lac promoter), this construction, designated pHGH 207, permits expression of the gene for tetracycline resistance under the control of the tryptophan promoter-operator. Thus the ligation mixture was transformed into E. coli 294 and colonies selected on LB plates containing 5 μg/ml tetracycline.

Plasmid pHGH207 was Eco RI digested and the trp promoter containing a 300 b.p. Eco RI fragment recovered by PAGE followed by electroelution. The 300 b.p. Eco RI fragment contains the E. coli trp promoter, operator, and trp leader ribosome binding site but lacks an ATG sequence for initiation of translation. This DNA fragment was cloned into the Eco RI site of pLe-IF A. The construction of the fragment is described in detail in (36).

2. The Tryptophan Control Element

The trp fragment just referred to is an analog of the E. coli tryptophan operon from which the so-called trp attenuator has been deleted, See (36), to controllably heighten expression levels. Expression plasmids containing the modified trp regulon can be grown to predetermined levels in nutrient media containing additive tryptophan in quantities sufficient to repress the promoter-operator system, then be deprived of tryptophan so as to derepress the system and occasion the expression of the intended product (36).

3. Detailed Description

More particularly, and with reference to FIG. 6, 250 μg of plasmid pL31 were digested with Pst I and the 1000 b.p. insert isolated by gel electrophoresis on a 6 polyacrylamide gel. Approximately 40 μg of insert was electroeluted from the gel and divided into 3 aliquots for further digestion: (a) A 16 μg sample of this fragment was partially digested with 40 units of Bgl II for 45' at 37° C. and the reaction mixture purified on a 6 polyacrylamide gel. Approximately 2 μg of the desired 670 b.p. fragment were recovered. (b) Another sample (8 μg) of the 1000 b.p. Pst I insert was restricted with Ava II and Bgl II. One μg of the indicated 150 b.p. fragment was recovered after gel electrophoresis. (c) 16 μg of the 1000 b.p. piece was treated with Sau 3a and Ava II. After electrophoresis on a 10 polyacrylamide gel, approximately 0.25 μg (~10 pmole) of the 34 b.p. fragment was recovered. The two indicated deoxyoligonucleotide, 5'-dAATTCATGTGT (fragment 1) and 5'-d CATCACACATG (fragment 2) were synthesized by the phosphortriester procedure (24). Fragment 2 was phosphorylated as follows. 200 μl (~40 pmol) of ($\gamma^{32}$P) ATP (Amersham, 5000 Ci/mmole) was dried down and resuspended in 30 μl of 60 mM Tris-HCl (pH8), 10 mM MgCl$_2$, 15 mM β-merceptoethanol, containing 100 pmoles of DNA fragment and 2 units of T4 polynucleotide kinase. After 15 minutes at 37° C., 1 ||1 of 10 mM ATP was added and the reaction allowed to proceed another 15 minutes. The mixture was then heated at 70° C. for 15 minutes, combined with 100 pmole of 5'-OH fragment 1 and 10 pmole of the 34 b.p. Sau 3a-Ava II fragment. Ligation was performed for 5 hours at 4° C. in 50 μl of 20 mM Tris-HCl (pH7.5) 10 mM Mg Cl$_2$, 10 mM dithiothreitol, 0.5 mM ATP and 10 units T4 DNA ligase. The mixture was electrophoresed on a 6 polyacrylamide gel and the 45 b.p. product recovered by electroelution. 860,000 Cerenkov cpm were recovered (~30 ng, 1 pmole), combined with 0.5 μg (5 pmoles) of the 150 b.p. Ava II-Bgl II fragment and 1 μg (2 pmoles) of the 670 b.p. Bgl II-Pst I fragment. The ligation was performed at 20° C. for 16 hours using 20 units of T4 DNA ligase. The ligase was inactivated by heating to 65° C. for 10 minutes. The mixture was then digested with ECo RI and Pst I to eliminate polymers of the gene. The mixture was purified by 6 percent polyacrylamide gel electrophoresis. 36,000 cpm (~0.04 pmole, 20 ng) of 865 b.p. product were isolated. One-half (10 ng) of this was ligated into pBR322 (0.3 μg) between the Eco RI and Pst I sites. Transformation of E. coli 294 gave 70 tetracycline resistant, ampicillin sensitive tranformants. Plasmid DNA isolated from 18 of these transformants was digested with Eco RI and Pst I. 16 of the 18 plasmids had an Eco RI-Pst I fragment 865 b.p. in length. One μg of one of these, pLe-IF A1, was digested with Eco RI and ligated to a 300 b.p. Eco RI fragment (0.1 μg) containing the E. coli trp promoter and trp leader ribosome binding site, prepared as described above. Transformants containing the trp promoter were identified using a $^{32}$P-trp probe in conjunction with the Grunstein-Hogness colony screening procedure (27). An asymetrically located Xba I site in the trp fragment allowed determination of recombinants in which the trp promoter was oriented in the direction of the Le-IF A gene.

K. Induction of Interferon Expression and In Vitro Assay

Extracts were prepared for IF assay as follows. One ml cultures were grown in L broth containing 5 μg/ml tetracycline to an A$_{550}$ of about 1.0, then diluted into 25 ml of M9 media containing 5 μg/ml tetracycline. 10 ml samples were harvested by centrifugation when A$_{550}$ reached 1.0 and cell pellets were suspended in 1 ml of 15 percent sucrose, 50 mM Tris-HCl (pH 8.0), 50 mM EDTA. One mg of lysozyme was added and, after 5 minutes at 0° C., cells were disrupted by sonication. The samples were centrifuged 10 minutes at 15,000 rpm in a Sorvall SM-24 rotor. Interferon activity in the supernatants was determined by comparison with Le-IF standards by the sytopathic effect (CPE) inhibition assay (2). To determine the number of IF molecules per cell a Le-IF specific activity of $4\times 10^8$ units/mg was used (7).

As shown in Table 1, Clone pLe-IF A trp 25, in which the trp promoter was inserted in the desired orientation, gives high levels of activity (as high as $2.5\times 10^8$ units per liter). As shown in Table 2, the IF produced by E. coli K-12 strain 294/pLe-IF A trp 25 behaves like authentic human Le-IF; it is stable to treatment at pH2 and is neutralized by rabbit anti-human leukocyte antibodies. The interferon has an apparent molecular weight of approximately 20,000.

L. In Vivo Antiviral Activity of Le-IF A

The in vivo efficacy of interferon requires the presence of macrophages and NK cells and the in vivo mode of action appears to involve stimulation of these cells (33). Thus, it remained possible that the interferon produced by E. coli 294/pLe-IF A25, while having antiviral activity in the cell culture assay, would not be active in infected animals. Moreover, the in vivo antiviral activity of the bacterially produced, nonglycosylated Le-IF A might be different from the glycosylated Le-IF derived from human "buffy coat" leukocytes. Therefore the biological activity of bacterially synthesized Le-IF A (~2 Pure) was compared with buffy coat Le-IF (~8 percent pure) in lethal encephalyomyocarditis (EMC) virus infection of squirrel monkeys (Table 3).

TABLE 1

Interferon activity in extracts of E. coli

| E. coli K-12 strain 294 transformed by: | Cell density (cells/ml) | IF Activity units/ml culture | Le-IF molecules per cell |
|---|---|---|---|
| pLe-IF A trp 25 | $3.5 \times 10^8$ | 36,000 | 9,000 |
| pLe-IF A trp 25 | $1.8 \times 10^9$ | 250,000 | 12,000 |

TABLE 2

Comparison of activities of extracts from E. coli 294/pLe-IF A25 with standard Le-IF

| | Interferon Activity (units/ml) | | |
|---|---|---|---|
| | untreated | pH2 | rabbit anti-human leukocyte antibodies |
| 294/pLeIF-A trp 25 extract | 500 | 500 | <10 |
| Le-IF standard | 500 | 500 | <10 |

The 250,000 U/ml extract of E. coli 294/pLe-IF A trp 25 described in Table 1 was diluted 500-fold with minimal essential medium giving a specific activity of 500 U/ml. A leukocyte interferon standard (Wadley Institute) previously titrated against the NIH leukocyte interferon standard, was also diluted to a final concentration of 500 U/ml. One ml aliquots were adjusted to pH 2 with 1N HCl, incubated at 4° C. for 52 hours, neutralized by addition of NaOH and IF activity determined by the standard CPE inhibition assay. 25 μl aliquots of the 500 U/ml samples (untreated) were incubated with 25 μl of rabbit anti-human leukocyte interferon for 60 at 37° C., centrifuged at 12,000×g for 5 minutes and the supernatant assayed.

TABLE 3

Antiviral effect of various Le-IF preparations against EMC virus infection of squirrel monkeys

| Treatment | Survivors | Serum p.f.u./ml. | | |
|---|---|---|---|---|
| | | day 2 | day 3 | day 4 |
| Control (bacterial proteins) | 0/3 | 10, 0, 0 } 3 | $3 \times 10^4$, 0, 0 } $10^4$ | $>10^5$, 1,200, 0 } $>3.4 \times 10^4$ |
| Bacterial Le-IF A | 3/3 | 0, 0, 0 | 0, 0, 0 | 0, 0, 0 |
| Le-IF standard | 3/3 | 0, 0, 0 | 0, 0, 0 | 0, 0, 0 |

All monkeys were male (average weight 713 g) and had no EMC virus antibodies prior to infection. The monkeys were infected intramuscularly with $100 \times LD_{50}$ EMC virus (determined in mice). The control treated monkeys died at 134, 158 and 164 hours post-infection. Interferon treatments of $10^6$ units were by the intravenous route at −4, +2, 23, 29, 48, 72, 168 and 240 hours, relative to infection. The bacterial leukocyte interferon was a column chromatography fraction from a lysate of E. coli 294/pLe-IF A25 at a specific activity of $7.4 \times 10^6$ U/mg protein. The control bacterial proteins were an equivalent column fraction from a lysate of E. coli 294/pBR322 at twice the total protein concentration. The leukocyte interferon standard was Sandai virus induced interferon from normal human "buffy-coat" cells, purified chromatographically to a specific activity of $32 \times 10^6$ U/mg protein.

The control monkeys showed progressive lethargy, loss of balance, flaccid paralysis of the hind-limbs and watering of the eyes commencing around 8 hours prior to death. The interferon treated monkeys showed none of these abnormalities; they remained active at all times and developed no viremia (Table 3). The one monkey in the control group which did not develop viremia by 4 days died latest (164th post-infection) but showed high titers of virus in the heart and brain on post-mortem. The interferon treated monkeys did not develop antibodies to EMC virus as determined 14 and 21 days after infection. These results demonstrate that the antiviral effects of Le-IF preparations in the infected animals can be attributed solely to interferon because the contaminating proteins are quite different in the bacterial and buffy coat preparations.

M. Isolation of cDNAs for Additional Leukocyte Interferons

DNA from the fully characterized Le-IF A cDNA-containing plasmid was excised with Pst I, isolated electrophoretically, and labelled by a published procedure (26) with $^{32}P$. The resulting radioactively labelled DNA was used as a probe to screen additional E. coli 294 transformants, obtained identically as those in Part D, by an in situ colony screening procedure (27). Colonies were isolated which hybridized in varying amounts to the probe. Plasmid DNA from these colonies and the ten hybridizing colonies referred to in Part I above was isolated by Pst cutting and characterized by three different methods. First, these Pst fragments were characterized by their restriction endonuclease digestion patterns with the enzymes Bgl II, Pvu II, and Eco RI. This analysis allowed the classification of at least eight different types (Le-IF A, Le-IF B, Le-IF C, Le-IF D, Le-IF E, Le-IF F, Le-IF G and Le-IF H), shown in FIG. 5, which approximates the location of various restriction cuts relative to the by-now known presequence and coding sequence of Le-IF A. One of these, Le-IF D, is believed to be identical to that reported in (39).

Secondly, certain of the DNAs were tested by a published hybridization selection assay (38) for the ability to selectively remove Le-IF mRNA from poly-A containing KG-1 cell RNA. Le-IF A, B, C and F were positive by this assay. Third, the latter Pst fragments were inserted in an expression plasmid, *E. coli* 294 transformed with the plasmid, and the fragments expressed. The expression products, believed to have been preinterferons, were all positive by CPE assay for interferon activity, albeit marginally active in the case of the Le-IF-F fragment. In addition to the foregoing, all of the Le-IF types described have been sequenced (See FIG. 3).

N. Direct Expression of a Second Mature Leukocyte Interferon

Figure 7A:
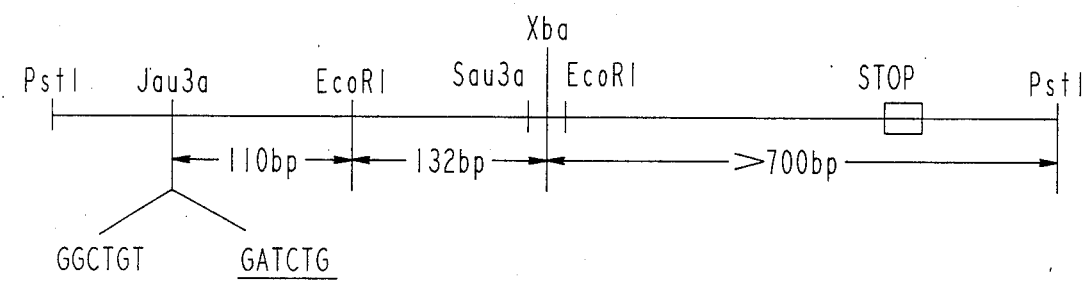
FIG. 7 (not to scale) schematically depicts a restriction map of two gene frgments employed in expressing the mature leukocyte interferon Le-IF B. The codon sequences indicated are the coding strand terminii resulting from digestion with the restriction enzyme Sau 3a in the two cases shown.
Figure 7B:
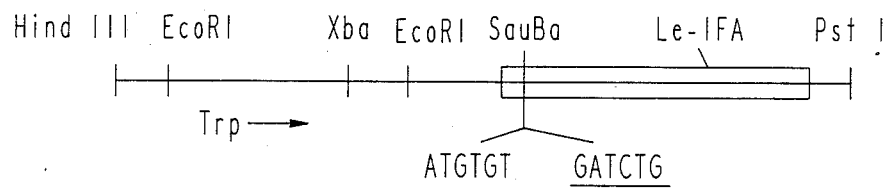

The sequence of the isolated fragment comprising the gene for mature Le-IF-B shows the first fourteen nucleotides of types A and B to be identical. We accordingly proposed to isolate a fragment from pLe-IF A25 bearing the trp-promoter-operator, ribosome binding site and the start of the Le-IF (A=B) gene, and combine this with the remaining portion of the B sequence in an expression plasmid. The salient restriction maps for the Pst fragment of pL4 (a plasmid comprising the Le-IF B Pst-ended gene depicted in FIG. 5) and pLe-IF A25 are shown, respectively, in FIGS. 7a and 7b.

To obtain the approximately 950 b.p. Sau 3a to Pst I fragment from the sequence shown in FIG. 7a several steps were necessary because of the presence of one or more intervening Sau 3a restriction sites, i.e.:

1. The following fragments were isolated:
   (a) 110 g b.p. from Sau 3a to Eco RI;
   (b) 132 b.p. from Eco RI to Xba;
   (c) >700 b.p. from Xba to Pst.
2. Fragments (1a) and (1b) were ligated and cut with Xba and Bgl II to preclude self-polymerization through Sau 3a and Xba end terminals (the relevant Sau 3a site was within a Bgl II site; Bgl II cuts to leave a Sau 3a sticky end). A 242 b.p. fragment was isolated.
3. The product of (2) and (1c) were ligated and cut with Pst I and Bgl II, again to prevent self-polymerization. An approximate 950 b.p. fragment, Sau 3a to Pst I of FIG. 7a, was isolated. This fragment comprised that portion of the Le-IF B gene not common to Le-IF A.
4. An approximate 300 b.p. fragment (Hind III to Sau 3a) comprising the trp promoter-operator, ribosome-binding site, ATG start signal and cysteine codon of Le-IF A was isolated from pLe-IF A25.
5. An approximately 3600 b.p. fragment Pst I to Hind III was isolated from pBr 322. This comprised the replicon and encoded tetracycline but not ampicillin resistance.
6. The fragments obtained in steps 3, 4 and 5 were triple-ligated and the resulting plasmid transformed into *E. coli* K-12 strain 294.

Transformants were miniscreened (37) and plasmid samples were digested with Eco RI. Digests yielded three fragments characteristic of:

(1) The Eco RI-Eco RI trp promoter fragment; (2) The internal Eco RI to Eco RI fragment of pL4; and (3) protein translational start signal to Eco RI fragment of pL4.

In CPE assay, bacterial extracts from clones made in the foregoing fashion typically assay at about $10 \times 10^6$ units interferon activity per liter at $A_{550}=1$. One representative clone prepared in this manner is 294/pLIF B trp 7.

O. Direct Expression of Further Mature Leukocyte Interferons

Additional full-length gene fragments that comprise other Le-IF types may be tailored and placed in expression vehicles for expression as in the case of Le-IF A. Complete sequencing by conventional means will reveal whether a restriction site lies sufficiently near the first amino acid codon of the mature interferon type as to permit convenient resort to the approach employed in part J, supra, for the expression of mature Le-IF A, i.e., elimination of the presequence by restriction cutting and replacement of codons for the N-terminal amino acids lost in presequence elimination by ligation of a synthetic DNA fragment. Failing that, the procedure described in (36) may be employed. Briefly, this entails cleaving the presequence-containing fragment precisely before the point at which the codon for the first amino acid of the mature polypeptide begins, by:

1. converting the double stranded DNA to single-stranded DNA in a region surrounding that point;
2. hybridizing to the single-stranded region formed in step (a) a complementary primer length of single-stranded DNA, the 5' end of the primer lying opposite the nucleotide adjoining the intended cleavage site;
3. restoring that portion of the second strand eliminated in step 1 which lies in the 3' direction from the primer by reaction with DNA polymerase in the presence of adenine, thymine, guanine and cytosine-containing deoxynucleotide triphosphates; and
4. digesting the remaining single-stranded length of DNA which protrudes beyond the intended cleavage point.

A short length of synthetic DNA terminating, at the 3' end of the coding strand, with the translation start signal ATG can then be ligated by, e.g., blunt-end ligation to the resulting tailored gene for the mature interferons and the gene inserted into an expression plasmid and brought under the control of a promoter and its associated ribosome binding site.

In a manner similar to that employed in part N, supra, gene fragments encoding Le-IF-C and Le-IF-D were appropriately configured for direct bacterial expression. The expression strategy for these additional leukocyte interferons included, in each case, resort to the approximately 300 b.p. fragment (Hind III to Sau 3a) comprising the trp promoter-operator, ribosome binding site, ATG start signal and cysteine codon of Le-IF A from pLe-IF A25. To this were combined gene fragments from the additional interferon genes encoding their respective amino acid sequences beyond the initial cysteine common to all. Each resulting plasmid was used to transform E. coli K-12 strain 294. Ligations to form the respective genes were as follows:

Le IF-C

Isolate the following fragments from pLe IF-C:
(a) 35 b.p. from Sau 3a to Sau 96
(b) >900 b.p. Sau 96 to Pst
(c) Isolate an approximate 300 b.p. fragment (Hind III-Sau 3a) from pLe IF A-25 as in part N (4) supra.
(d) Isolate the approximately 3600 b.p. fragment of part N (5) supra.

Construction (1) Ligate (a) and (c). Cleave with Bgl II, Hind III and isolate the approximately 335 b.p. product.

(2) Triple ligate (l)+(b)+(d) and transform E. coli with the resulting plasmid.

A representative clone made in this manner is E. coli K-12 strain 294/pLe IF C trp 35.

Le-IF D

Isolate from pLe IF-D:
(a) 35 b.p. from Sau 3a to Ava II
(b) 150 b.p. from Ava II to Bgl II
(c) approx. 700 b.p. from Bgl II to Pst
Isolate from pLe IF A25:
(d) 300 b.p. from Hind III to Sau 3a
Isolate from PBr 322:
(e) approx. 3600 b.p. from Hind III to Pst

Construction (1) ligate (a)+(b), cut with Bgl II and purify a 185 b.p. product (1).

(2) ligate (l)+(d), cut with Hind III, Bgl II, and purify the approx. 500 b.p. product (2).

(3) ligate (2)+(c)+(e) and transform E. coli with the resulting plasmid.

A representative cone made in this manner is E. coli K-12 strain 294/pLeIF D trp 11.

Le-IF F

The Le-IF F containing fragment may be tailored for direct expression through reassembly made convenient by the complete homology of amino acids 1–13 of Le-IF B and Le-IF F. A trp promoter-containing fragment (a) with appropriately configured ends is obtained from pHGH 207, described above, via Pst I and Xba I digestion followed by isolation of the ca. 1050 b.p. fragment. A second fragment (b) is obtained as the larger of the fragments resulting from Pst I and Bgl II digestion of the plasmid pHKY 10 (36). Fragment (a) contains approximately half the gene encoding amplicillin resistance; fragment (b) contains the remainder of that gene and the entire gene for tetracycline resistance save for the associated promoter. Fragments (a) and (b) are combined via T4 ligase and the product treated with Xba I and Bgl II to eliminate dimerization, forming a fragment (c) comprising the trp promoter-operator and genes for tetracycline and ampicillin resistance.

A fragment (d) of approximately 580 b.p. is obtained by Ava II and Bgl II digestion of pLe IF-F. This comprises codons for amino acids 14–166 of Le-IF F.

A fragment (e) (49 b.p.) is obtained by Xba I and Ava II digestion of pLe-IF B. Fragment (e) encodes amino acids 1–13 of Le-IF F.

Fragments (c), (d) and (e) are triple ligated in the presence of T4 ligase. The cohesive ends of the respective fragments are such that the composite plasmid circularizes correctly, bringing the tetracycline resistance gene under the control of the trp promoter-operator along with the gene for mature Le-IF F, such that bacteria transformed with the desired plasmid may be selected on tetracycline-containing plates. A representative clone prepared in this manner is E. coli K-12 strain 294/pLeIF F trp 1.

Le-IF H

The complete Le-IF H gene may be configured for expression as a mature leukocyte interferon as follows:

1. Plasmid pLe-IF H is subjected to Hae II and Rsa I digestion with isolation of the 816 base pair fragment extending from the signal peptide amino acid 10 to the 3' noncoding region.

2. The fragment is denatured and subjected to repair synthesis with Klenow fragment, Klenow et al., Proc. Natl. Acad. Sci. (USA) 65, 168 (1970), employing the synthetic deoxyribooligonucleotide primer 5'-dATG TGT AAT CTG TCT. This general procedure is also described by Goeddel et al., U.S. Ser. No. 190799, filed Sept. 25, 1980.

3. The resulting product is cleaved with Sau 3a and a 452 base pair ("bp") fragment representing amino acids 1 to 150 isolated.

4. Sau 3a and Pst I digestion of pLeIF H and isolation of the resulting 500 b.p. fragment yields a gene encoding amino acids 150 through the end of the coding sequence.

5. Fragments isolated in steps (3) and (4) are ligated to form a fragment:

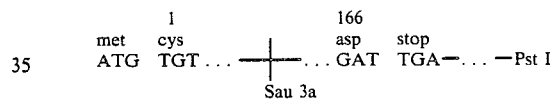

encoding the 166 amino acids of Le-IF H.

6. pLeIF A trp 25 is digested with Xba I, blunt-ended with DNA polymerase I and theproduct digested with Pst I. The large resulting fragment may be isolated and ligated with the product of step (5) to form an expression plasmid capable, upon transformation of E. Coli K-12 strain 294 or other host bacteria, of expressing mature Le-IF H.

LeIF-I

The phage λ Charon 4A recombinant library of the human genome constructed by Lawn et al., Cell 15, 1157 (1978), was screened for leukocyte interferon genes by procedures described by Lawn et al., Supra and Maniatis et al., Cell 15, 687 (1978). A radioactive LeIF probe derived from the cDNA clone LeIF A (Goeddel et al., Nature 287, 411 (1980), was used to screen approximately 500,000 plaques. Six LeIF genome clones were obtained in this screening. Following rescreening and plaque purification, one of these clones, λHLeIF2, was selected for further analysis.

Using the method described above, other probes can be used to advantage to isolate additional LeIF clones from the human genome. These, in turn, can be employed to produce additional leukocyte interferon proteins in accordance with this invention.

1. The 2000 base pair Eco RI fragment of the genomic clone (λHLeIF2) was subcloned into pBR325 at the Eco RI site. The resulting plasmid LeIF I was cleaved with Eco RI and the 2000 base pair fragment isolated. The deoxyoligonucleotide dAATTCTGCAG (an Eco RI>Pst I convertor) was ligated to the 2000 base pair Eco RI fragment and the resulting product cleaved with Pst I to give a 2000 base pair fragment containing Pst I ends. This was cleaved with Sau 96 and a 1100 base pair fragment isolated which has one Pst I end and one Sau 96 end.

2. The plasmid pLeIF C trp 35 was digested with Pst I and Xba I. The large fragment was isolated.

3. The small Xba I-Pst I fragment from pLeIF C trp 35 was digested with Xba I and Sau 96. A 40 base pair Xba I-Sau 96 fragment was isolated.

4. The fragments isolated in steps (1), (2) and (3) were ligated to form the expression plasmid pLeIF I trp 1.

LeIF-J

1. The plasmid pLeIF J contains a 3.8 kilobase Hind III fragment of human genomic DNA which includes the LeIF J gene sequence. A 760 base pair Dde I-Rsa I fragment was isolated from this plasmid.

2. The plasmid pLeIF B trp 7 was cleaved with Hind III and Dde I and a 340 bp Hind III-Dde I fragment isolated.

3. The plasmid pBR322 was cleaved with Pst I, blunt ended by incubation with DNA Pol I (Klenow fragment), then digested with Hind III. The large (~3600 bp) fragment was isolated.

4. Fragments isolated in steps (1), (2) and (3) were ligated to form the expression plasmid pLeIF J trp 1.

Le IF-K and L

Screening of the phage λ Charon 4A recombinant library of the human genome, supra, by in situ plaque hybridization (Benton and Davis, Science 196, 180 (1977)) with the radioactive LeIF probe described above provided a further positive clone which appeared distinct. This clone (G8) provided the following ECORI fragments: 3.3, 3.1, 2.9, 2.2, 1.4 and 1.3 kilobase pairs of which the 2.2, 1.4 and 1.3 fragments hybridized to the radiolabeled cDNA probe (Goeddel et al., supra) after separation by 0.8% agarose gel electrophoreus followed by transfer to nitrocellulose filter paper.

Figure 11:
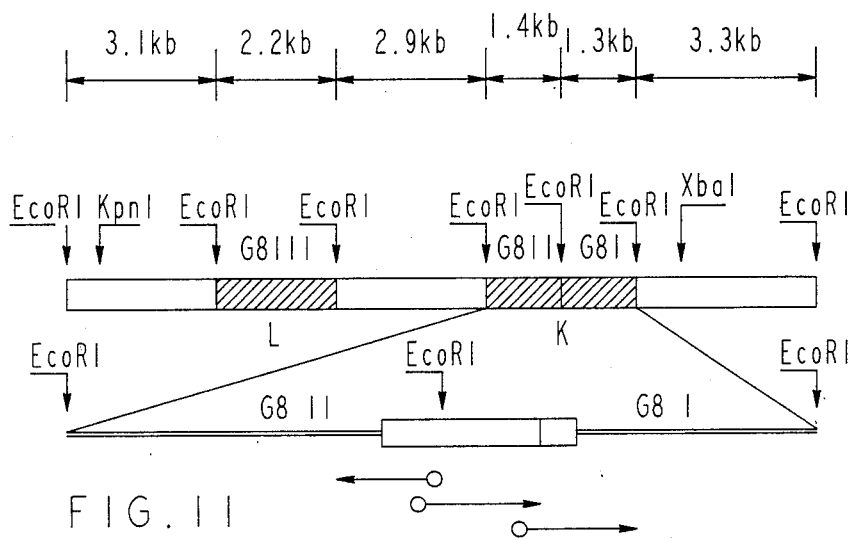
FIG. 11 shows the restriction enzyme cleavage sites on the 14-kb insert of genomic DNA clone G8.

FIG. 11 shows a map of restrictio enzyme cleavage sites on the 14-kb insert of genomic DNA clone G8. The three fragments hybridizing to the leukocyte interferon cDNA were sequenced with internal primers obtained from plasmid 104 containing interferon cDNA sequences (Maeda et al., Proc. Natl. Acad. Sci. U.S.A. 77, 7010 (1980) or to a synthetic oligonucleotide primer complementary to the M13 DNA region preceding the ECORI site as shown in FIG. 11.

In FIG. 11 vertical arrows indicate the restriction enzyme cleavage sites. Hatched boxes represent the ECORI fragments hybridizing to the cDNA probe. A solid box represents the protein-coding region. Horizontal arrows represent the direction and length of dideoxynucleotide termination sequencing reaction initiating from the primers indicated by open circles.

The total DNA sequence of the human Le IF K and L genes are shown in FIGS. 10A and 10B. The amino acid sequence is presented above the nucleotide sequence.

PROTOCOL FOR EXPRESSION OF IFLrK

The following fragments are isolated to construct an expression plasmid for IFLrK:

(a) An approximate 300-bp fragment (HindIII-Sau3A) containing the trp operator promoter, ATG start codon and cysteine codon of IFLrA (pLIF-A25).

(b) An approximate 99-bp fragment (EcoRI-Sau3A) from the fragment designated λG8-II (1.4 kb) containing the amino-terminal coding portion of ILF-G8-1 (a genomic DNA isolated from the human gene library).

(c) The fragment designated λG8-I of approximate 1.3 kb containing the carboxy-terminal coding portion of IFL-G8-1 (EcoRI-EcoRI).

(d) An EcoRI-HindIII fragment from pBR322(4.3 kb) containing the replicon and coding region for ampicillin and tetracycline resistance.

Step 1:

Fragment (a) is ligated to fragment (d) to yield a 4.6 kb linear fragment (Sau3A-EcoRI). This is ligated to fragment (b) to yield a circular molecule. The above ligations are performed simultaneously as a 3-piece ligation. Transformants are selected for ampicillin and tetracycline resistance. Transformants from Step 1 are screened by restriction mapping and a clone selected for further work. The correct molecule has 3 EcoRI sites.

Step 2:

The plasmid from Step 1 is partially digested with EcoRI and the linear form isolated by gel electrophoresis. The linear EcoRI fragment is ligated to fragment (c). With 3 sites of insertion and 2 orientations possible, one-sixth of the resultant transformants are in the proper configuration to produce leukocyte interferon K (IFLrK).

Summary of the Recombinant Plasmid pIFLrK:

The recombinant plasmid, pIFLrK, was constructed as summarized above. Upon transformation into *E. coli* K-12, this plasmid produces a protein of 166 amino acids equivalent to one of the species of human leukocyte interferon in addition to $NH_2$-terminal methionine (initiation codon).

Figure 12:
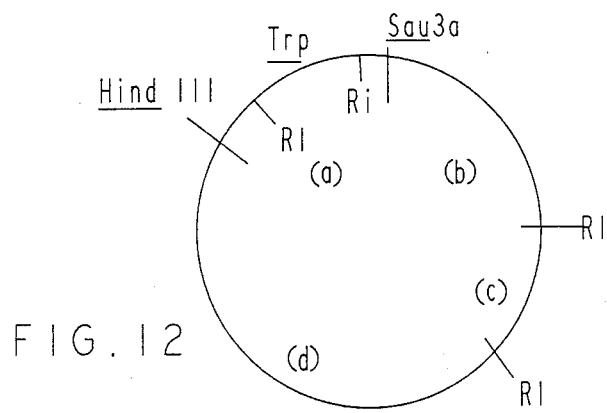
FIGS. 12 and 13 show the construction of the recombinant plasmid pIFLrK and pIFLrL respectively.

The plasmid contains the fragments indicated in FIG. 12.

The interferon sequence codes for a protein consistent with protein sequence data derived from purified human leukocyte interferons (Rubinstein et al., *Arch. Biochem. Biophys.*, in press (1981); Levy et al., *Proc. Natl. Acad. Sci. U.S.A.*, in press (1981); Levy et al., *Proc. Natl. Acad. Sci. U.S.A.* 77, 5102–5104 (1980); Zoon et al., *Science* 207, 527–528 (1980). The remainder of the DNA contains 3'-untranslated portions of the gene, but contains no other genes.

PROTOCOL FOR EXPRESSION OF IFLrL

Isolate the following fragments:

(a) 35-bp Sau3a to Sau96I fragment from G8-III (2.2 kb).

(b) Sau96I to EcoRI fragment to 3'-end of G8-III segment (about 1,300 bp).

(c) approximate 300-bp fragment (HindIII-Sau3a) from pLeIFA-25 as above.

(d) isolated HindIII-EcoRI fragment (4.3 kb) from pBR322 as above.

Figure 13:
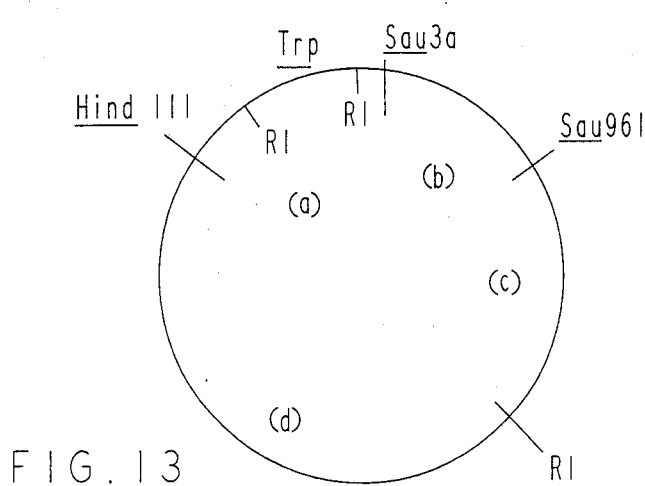

Step 1:

Fragment (a) is ligated to fragment (b) and (c) in three-part ligation mixture; the resulting a-b-c segments are cleaved with HindIII and EcoRI to minimize polymerization. The isolated segment c-a-b is ligated to (d) to yield the expression plasmid. Transformants are selected for ampicillin and tetracycline resistance. Transformations are screened by restriction mapping. The correct molecule has a size of approximately 6,000 bp, three EcoRI sites, and upon transformation into *E. coli* K12 produces a protein (IFLrL) of 166 amino acids that is equivalent to one of the species of human leukocyte interferon in addition to the NH$_2$-terminal methionine (initiation codon). The plasmid contains the fragments indicated in FIG. 13.

The interferon sequence codes for a protein consistent with protein sequence data derived from purified human leukocyte interferons (Rubinstein et al., *Arch. Biochem. Biophys.*, in press [1981]; Levy et al., *Proc. Natl. Acad. Sci. U.S.A.*, in press [1981]; Levy et al., *Proc. Natl. Acad. Sci. U.S.A.* 77, 5102–5104 [1980]; Zoon et al., *Science* 207, 527–528 [1980]). The remainder of the DNA contains 3'-untranslated portions of the gene, but contains no other genes.

P. Purification

The content of leukocyte interferon in bacterial extracts may be enhanced by successive:

1. polyethylene-imine precipitation, in which most of the cellular protein, including the interferon, remains in the supernatant;
2. ammonium sulfate fractionation, in which interferon comes out of solution in 55 saturated ammonium sulfate;
3. suspension of the ammonium sulfate pellet in 0.06M potassium phosphate, 10 mM tris-HCl, pH 7.2, and dialysis against 25 mM tris-HCl, pH 7.9 (interferon activity remains in solution); and
4. Loading the above supernatant, pH adjusted to 8.5, on a DEAE-cellulose (Whatman DE-53) column and eluting with a linear gradient of 0 to 0.2M NaCl in 25 mM tris HCl, pH 8.5.
5. Adsorption on Cibachrome Blue Agarose (Amicon Blue A) or hydroxyapatitie and elution with high salt (1.5M KCl or 0.2M phosphate respectively)—optional.
6. Molecular sizing on a Sephadex G-75 column.
7. Cation exchange chromatography on CM-cellulose (Whatman CM-52) in 25 nM ammonium acetate at pH 5.0, developed with an ammonium acetate gradient (to 0.2M ammonium acetate).

In our hands, the above process gives essentially homogeneous material (e.g. >95 percent pure).

The material can also be further purified by further steps such as, in succession:

8. Size exclusion chromatography;
9. Reverse phase (RP-8) high pressure liquid chromatography; and if desired
10. Affinity chromatography on immobilized antiinterferon antibodies.

Affinity chromatography on a monoclonal antibody column can be used as an alternative to the Step 6 Sephadex G-75 column above. The material from step 4 is loaded on the monoclonal antibody column, prepared as described by Milstein, C., *Scientific American* 243, No. 4, p. 66 (1980), and eluted with 0.2M acetic acid, 0.1 percent triton and 0.15M NaCl.

In an alternative, preferred embodiment, the leukocyte interferon produced by the procedures described herein can be purified by the following steps:

1. Frozen cell pellets containing the expressed leukocyte interferon are broken up manually or by appropriate size reduction equipment. The partially thawed cells are suspended in 4 volumes of buffer A. The suspension is held to approximately 4° C.

Buffer A:
0.1M Tris adjusted to pH 7.5–8.0
10% (w/v) sucrose
0.2M NaCl
5 mM EDTA
0.1 mM PMSF
10–100 mM MgCl$_2$ The suspension is passed through a Manton Gaulin laboratory homogenizer at about 6000 psi followed by a second pass at less than 1000 psi. Effluent from the homogenizer from both passes is cooled in an ice bath.

2. Polyethylene-imine (PEI) (e.g. Polymin P) is added slowly to the homogenate to a concentration of about 0.35% and allowed to stand for about 30 min. The solids are removed by centrifugation or filtration. This step is temperature controlled or performed sufficiently quickly that the supernatant (filtrate) is kept at less than 10° C. The supernatant (filtrate) is concentrated by ultrafiltration, e.g. on a Millipore Pellicon cassette system (PTGC, 5 ft.$^2$, MWCO 10,000), to approximately 1/10 the original volume. Particulate matter or haziness in the retentate may be removed by an appropriate filter such as a microporous membrane.

3. The clarified solution is loaded directly onto a monoclonal antibody column at a flux of 5–8 cm/hr. (e.g. 25–40 ml/hr. on 2.6 cm Diam column). After loading the column is washed with approximately 10 column volumes of 25 mM Tris HCl, pH 7.5–8.5 including NaCl (0.5M) and surfactant such as Triton X-100 (0.2%) or equivalent. Following the wash the column is rinsed with about 10 column volumes of solution containing 0.15M NaCl and surfactant such as Triton X-100 (0.1%) or equivalent. The column is eluted with 0.2M acetic acid containing surfactant such as Triton X-100 (0.1%) or equivalent. The protein peak from the monoclonal antibody column (as determined by UV absorbence or other convenient assay) is pooled and the pII adjusted to approximately 4.5 with 1N NaOII or 1.0M Tris base.

4. The pooled interferon peak is loaded onto a cationic exchanger such as Whatman CM52 cellulose or equivalent which has been equilibrated with suitable buffer such as ammonium acetate pH 4.5 (50 mM). After loading, the column is washed with equilibrating buffer until the UV absorbence of the effluent has reached a plateau so that little additional protein is eluting from the column. The column is then eluted with 25 mM ammonium acetate/0.12M sodium chloride or a combination which optimizes recovery of interferon and affords a lyophilized cake having satisfactory appearance and solubility properties.

The monoclonal antibodies employed in the preferred embodiment described above can be prepared by the procedures described by Staehelin, et. al., *P.N.A.S.*, 78, pp. 1848–52 (1981). Monoclonal antibodies are purified and covalently linked to Affigel-10 as described below:

Preparation and Purification of Monoclonal Antibodies from Ascitic Fluid. Five female Balb/c mice were each inoculated with 5 to 10×10$^6$ hybridoma cells from mid-log growth phase. About 5×10$^6$ viable cells obtained from the mouse producing fluid were inoculated intraperitoneally into each of 10 or more mice. The ascitic fluid was collected repeatedly (2 to 4 times) from each mouse. Up to three transfers and collections may be performed from one group of mice to the next. Ascitic fluid from mice at each transfer was pooled.

Cells and debris were removed from the ascitic fluid by low speed centrifugation (500–1000×g) for 15 min. Then centrifugation was performed for 90 min. at 18,000 rpm in the SS34 Sorvall rotor without braking. The supernatant was frozen and stored at −20° C. After thawing, additional fibrin and particulate material were removed by centrifugation at 35,000 rpm for 90 min. in the Type 35 Spinco rotor. Batches of ascitic fluid from each transfer were tested for specific antibody activity by a solid phase antibody-binding assay (Staehelin, et. al., *P.N.A.S.*, 78, pp. 1848–52 (1981) and pooled if found satisfactory.

Concentration of protein in the pooled solutions was estimated by the approximation that 1 mg of protein yields an absorbance of 1.2 at 280 nm in a cuvette with a path length of 1.0 cm. Ascites fluids with high levels of antibody contain 30 to 35 mg protein/ml. This is equivalent to 4–7 mg of specific antibody/ml. The fluid was diluted with PBS (0.01M sodium phosphate, pH 7.3, 0.15M NaCl) to a protein concentration of 10 to 12 mg/ml (12 to 15 $A_{280}$ units/ml).

To each 100 ml of diluted solution, 90 ml of room temperature saturated ammonium sulfate solution was added slowly with vigorous stirring at 0° C. The suspension was kept in ice for 40 to 60 min., then centrifuged for 15 min. at 10,000 rpm in a Sorvall GS-A rotor at 4° C. The supernatant was decanted and drained well. The protein pellets were dissolved in 0.02M tris.HCl (pH 7.9)/0.04M NaCl (Buffer A; about 5 ml per 50 ml centrifuge bottle). The protein solution was dialyzed for 16 to 18 hrs. at room temperature against 100 volumes of Buffer A with at least one change of the buffer. The dialyzed solution was centrifuged at 15,000 rpm in a SS34 Sorvall rotor for 10 min. to remove undissolved material. About 30% to 35% of the original amount of total protein in the ascitic fluid was recovered as estimated by absorption at 280 nm.

The solution containing 30 to 40 mg of protein per ml was then applied to a column of DEAE-cellulose (DE52, Whatman) equilibrated with Buffer A. A column bed volume of at least 100 ml was used for each gram of protein applied. The antibody was eluted from the column with a linear NaCl gradient containing 0.02M Tris.HCl, pH 7.9, from 0.04M to 0.5M NaCl. Pooled peak fractions eluting between 0.06 and 0.1M NaCl were concentrated by precipitation with an equal volume of room temperature saturated ammonium sulfate and centrifugation. The protein pellets were dissolved in 0.2M $NaHCO_3$ (pH~8.0)/0.3M NaCl (Buffer B) followed by dialysis against three changes of the same buffer at room temperature. The dialyzed solutions were centrifuged at 20,000×g for 15 min. to remove any insoluble material. Protein concentration was adjusted to 20 to 25 mg/ml with Buffer B. SDS-polyacrylamide gel electrophoresis of representative monoclonal antibodies is shown in FIG. 1.

Preparation of Immunoadsorbants. Affigel-10 (BioRad Laboratories, Richmond, Calif.) was washed on a sintered glass filter three times with ice-cold isopropanol followed by three washes with ice-cold distilled water. The gel slurry (~50% in cold water) was transferred to plastic tubes and sedimented by a brief centrifugation. The supernatant was aspirated. The packed gel was mixed with an equal volume of purified antibody solution and rotated end-over-end at 4° C. for 5 hrs. After reaction, the gel was centrifuged, then washed twice with Buffer C (0.1M $NaHCO_3$/0.15M NaCl) to remove uncoupled antibody. Protein determination of the combined washes revealed that more than 90% of antibody was coupled to the gel.

To block unreacted sites, the gel was mixed with an equal volume of 0.1M ethanolamine.HCl (pH 8) and rotated end-over-end at room temperature for 60 min. The gel slurry was washed free of reactants with PBS and stored in PBS in the presence of 0.02% (w/v) sodium azide at 4° C.

Q. Parenteral Administration

Le-IF may be parenterally administered to subjects requiring antitumor, or antiviral treatment, and to those exhibiting immunosuppressive conditions. Dosage and dose rate may parallel that currently in use in clinical investigations of human derived materials, e.g., about $(1-10) \times 10^6$ units daily, and in the case of materials of purity greater than 1 percent, likely up to, e.g., $50 \times 10^6$ units daily. Preliminary indications in the monkey study described above suggest that dosages of bacterially obtained Le-IF could be significantly elevated for greater effect owing to the essential absence of human proteins other than Le-IF, which proteins in leukocyte-derived materials may act as pyrogens, exhibiting adverse effects, e.g., malaise, temperature elevation, etc.

As one example of an appropriate dosage form for essentially homogeneous bacterial Le-IF in parenteral form, 3 mg. Le-IF of specific activity of, say, $2 \times 10^8$ U/mg may be dissolved in 25 ml. 5N serum albumin (human)-USP, the solution passed through a bacteriological filter and the filtered solution aseptically subdivided into 100 vials, each containing $6 \times 10^6$ units pure interferon suitable for parenteral administration. The vials are preferably stored in the cold ($-20°$ C.) prior to use.

The compounds of the present invention can be formulated according to known methods to prepare pharmaceutically useful compositions, whereby the polypeptide hereof is combined in admixture with a pharmaceutically acceptable carrier vehicle. Suitable vehicles and their formulation are described in Remington's *Pharmaceutical Sciences* by E. W. Martin, which is hereby incorporated by reference. Such compositions will contain an effective amount of the interferon protein hereof together with a suitable amount of vehicle in order to prepare pharmaceutically acceptable compositions suitable for effective administration to the host. One preferred mode of administration is parenteral.

REFERENCES

1. Isaacs, A. and Lindenmann, J. *Proc. R. Soc.* B147, 258–267 (1957).
2. Stewart, W. E. II *The Interferon System,* Springer, New York (1979).
3. U.S. Pat. No. 3,699,222.
4. U.S. patent application Ser. No. 106,644 filed Dec. 26, 1979 by S. Pestka and M. Rubenstein, assigned to Hoffman LaRoche, Inc.
5. K. Itakura et. al, *Science* 198, 1056 (1971).
6. Cavalieri, R. L., Havell, E. A., Vileck, J. and Pestka, S. *Proc. Natn. Acad. Sci. U.S.A.* 74, 3287–3291 (1977).
7. Rubinstein, M., Rubinstein, S., Familletti, P. C., Miller, R.S., Waldman, A. A. and Pestka, S. *Proc. Natn. Acad. Sci. U.S.A.* 76, 640–644 (1979).
8. Zoon, K. C., Smith, M. E., Bridgen, P. J., zur Nedden, D. and Anfinsen, C. B. *Proc. Natn. Acad. Sci. U.S.A.* 76, 5601–5606 (1979).
9. D. V. Goeddel et. al, *Proc. National Academy of Sciences,* USA 76, 106 (1979).
10. G. B. Patent Publication No. 2 007 676A.
11. U.S. Pat. No. 190,495.
12. British patent publication No. 2055382A.
13. (No reference)
14. Chirgwin, J. M. et al (1979) *Biochemistry* 18, 5294.

15. Koeffler, H. P. and Golde, D. W. *Science* 200, 1153-1154 (1978).
16. Green, M. et. al (1976) *Arch. Biochem. Biophys.* 172, 74–89.
17. Wickens, M. P., Buell, G. N. and Schimke, R. T. *J. Biol. Chem.* 253, 2483-2495 (1978).
18. Goeddel, D. V., Heyneker, H. L., Hozumi, T., Arentzen, R., Itakura, K., Yansura, D. G., Ross, M. J., Miozzari, G., Crea, R. and Seeburg, P. H. *Nature* 281, 544-548 (1979).
19. Chang, A. C. Y., Nunberg, J. H., Kaufman, R. J., Erlich, H. A., Schmike, R. T. and Cohen, S. N. *Nature* 275, 617-624 (1978).
20. Bolivar, F., Rodriguez, R. L., Greene, P. J., Betlach, M. C., Heyneker, H. L., Boyer, H. W., Crosa, J. H. and Falkow, S. *Gene* 2, 95-113 (1977).
21. Okuyuma, A. et. al (1978) *Arch. Biochem. Biophys.* 188, 98.
22. Birnboim., H. C. and Doly, J. *Nucleic Acids Res.* 7, 1513-1523 (1979).
23. Kafatos, F. C., Jones, C. W. and Efstratiadis, A. *Nucleic Acids Res.* 7, 1541-1552 (1979).
24. Crea, R., Kraszewski, A., Hirose, T. and Itakura, K. *Proc. Natn. Acad. Sci. U.S.A.* 75, 5765-5769 (1978).
25. Noyes, B., Mevarech, M., Stein, R. and Agarwal, K. L. *Proc. Natn. Acad. Sci.* U.S.A. 76, 1770-1774 (1979).
26. Taylor, J. M., Illemensee, R. and Summers, S. *Biochim. Biophys. Acta* 442, 324-330 (1976).
27. Grunstein, M. and Hogness, D. S., *Proc. Natn. Acad. Sci. U.S.A.* 72, 3961-3965 (1975).
28. Wallace, R. B., Shaffer, J., Murphy, R. F., Bonner, J. and Itakura, K. *Nucleic Acids Res.* 6, 3543-3557 (1979).
29. Clewell, D. B. and Helinski, D. R. *Biochemistry* 9, 4428-4440 (1970).
30. Maxam, A. M. and Gilbert, W. *Methods Enzymol.* 65, 499-560 (1980).
31. Smith, A. J. H. *Methods Enzymol.* 65, 560-580 (1980).
32. Lillenhaug, J. R. et. al (1976) *Biochemistry* 15, 1858
33. Herberman, R. B., Djeu, J. V., Ortaldo, J. R., Holden, H. T., West, W. H. and Bonnard, G. D. *Cancer Treat. Rep.* 62, 1893-1896 (1978); Gidlund, M., Orn, A., Wigzell, H., Senik, A. and Gressor, I. *Nature* 273, 759-761 (1978); Stebbing, N., Dawson, K. M. and Lindley, I. J. D. *Infect. immun.* 19, 5-11 (1978).
34. Clewell, D. B. (1970) *Biochemistry* 9, 4428.
35. Radloff, R. et al (1967) *Proc. Natl. Acad. Sci. U.S.A.* 57, 1514. 136.
36. U.S. patent application Ser. No. 06/133,296 filed Mar. 24, 1980 by Dennis G. Kleid et. al, assigned to Genentech, Inc.
37. Birnboim, H. C. and Doly, J., *Nucleic Acids Research* 7, 1513 (1979)
38. Cleveland, D. W. et. al (1980) *Cell* 20, 95
39. Nagata, S. et al, *Nature* 284, 316 (1980)

We claim:

1. A polypeptide of about 166 amino acids comprising the amino acid sequence of human Le IF K as a mature human leukocyte interferon, microbially produced and unaccompanied by any corresponding presequence or portion thereof.

2. A polypeptide according to claim 1, unaccompanied by associated glycosylation.

3. The polypeptide according to claim 1, optionally containing the amino acid methionine attached to the N-terminus of the ordinarily first amino acid of said interferon.

4. A polypeptide of about 166 amino acids comprising the amino acid sequence of human Le IF L as a mature human leukocyte interferon, microbially produced and unaccompanied by any corresponding presequence or portion thereof.

5. A polypeptide according to claim 4, unaccompanied by associated glycosylation.

6. The polypeptide according to claim 4, optionally containing the amino acid methionine attached to the N-terminus of the ordinarily first amino acid of said interferon.

* * * * *